United States Patent
Haick et al.

(10) Patent No.: US 11,129,571 B2
(45) Date of Patent: Sep. 28, 2021

(54) CARDIAC WAVEFORM SENSING

(71) Applicant: TECHNION RESEARCH & DEVELOPMENT FOUNDATION LIMITED, Haifa (IL)

(72) Inventors: Hossam Haick, Haifa (IL); Meital Segev-Bar, Haifa (IL); Gady Konvalina, Haifa (IL)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 0 days.

(21) Appl. No.: 16/310,457

(22) PCT Filed: Jun. 14, 2017

(86) PCT No.: PCT/IL2017/050656
§ 371 (c)(1),
(2) Date: Dec. 17, 2018

(87) PCT Pub. No.: WO2017/216793
PCT Pub. Date: Dec. 21, 2017

(65) Prior Publication Data
US 2019/0328328 A1 Oct. 31, 2019

Related U.S. Application Data

(60) Provisional application No. 62/349,722, filed on Jun. 14, 2016.

(51) Int. Cl.
*A61B 5/02* (2006.01)
*A61B 5/00* (2006.01)
(Continued)

(52) U.S. Cl.
CPC .......... *A61B 5/6843* (2013.01); *A61B 5/0205* (2013.01); *A61B 5/7207* (2013.01);
(Continued)

(58) Field of Classification Search
CPC ..... A61B 2562/0261; A61B 5/00; A61B 5/72; A61B 5/7214; A61B 5/02
See application file for complete search history.

(56) References Cited

U.S. PATENT DOCUMENTS 3,880,145 A * 4/1975 Blick ..................... A61B 5/021
600/485
5,494,043 A * 2/1996 O'Sullivan ........ A61B 5/02208
600/500
(Continued)

FOREIGN PATENT DOCUMENTS

WO        9416610 A2    8/1994
WO    2013068955 A1    5/2013
(Continued)

*Primary Examiner* — Lynsey C Eiseman
(74) *Attorney, Agent, or Firm* — Roach Brown McCarthy & Gruber; Kevin D. McCarthy

(57) ABSTRACT

A sensing device that may include sensing elements that elements comprise a first sensing element, a second sensing element; wherein each sensing element comprises one or more piezoresistive materials; and a sensing circuit that is coupled to the sensing elements, wherein the sensing circuit is configured to sense a resistance of the first sensing element and of the second sensing element, and to determine, based on the resistance of the first sensing element and of the second sensing element, a first parameter of a cardiac waveform of a living being, wherein the cardiac waveform (a) is sensed by the first sensing element, and (ii) is not sensed by the second sensing element.

20 Claims, 24 Drawing Sheets

(51) Int. Cl.
  *A61B 5/0205* (2006.01)
  *G01L 1/18* (2006.01)
  *H05K 1/09* (2006.01)
  *H05K 3/12* (2006.01)
  *A61B 5/021* (2006.01)
  *A61B 5/024* (2006.01)

(52) U.S. Cl.
  CPC ............... *G01L 1/18* (2013.01); *H05K 1/097* (2013.01); *H05K 3/12* (2013.01); *A61B 5/02108* (2013.01); *A61B 5/02125* (2013.01); *A61B 5/02405* (2013.01); *A61B 2562/0252* (2013.01); *A61B 2562/046* (2013.01); *A61B 2562/164* (2013.01); *H05K 2201/10151* (2013.01); *H05K 2203/1131* (2013.01)

(56) References Cited

U.S. PATENT DOCUMENTS

| | | |
|---|---|---|
| 2003/0144829 A1 | 7/2003 | Geatz et al. |
| 2008/0266118 A1* | 10/2008 | Pierson ............... A61B 5/6826 340/573.6 |
| 2011/0077537 A1 | 3/2011 | Ebara et al. |
| 2012/0132930 A1 | 5/2012 | Young et al. |
| 2012/0209090 A1 | 8/2012 | Goodall et al. |
| 2015/0309563 A1 | 10/2015 | Connor |
| 2016/0011063 A1 | 1/2016 | Zhang et al. |
| 2016/0089042 A1* | 3/2016 | Saponas ............. A61B 5/02405 600/437 |

FOREIGN PATENT DOCUMENTS

| | | | |
|---|---|---|---|
| WO | 2015036647 A1 | 3/2015 | |
| WO | 2015086725 A1 | 6/2015 | |
| WO | 2015172897 A1 | 11/2015 | |
| WO | WO-2015172897 A1 * | 11/2015 | ............... G01L 1/18 |
| WO | 2016092494 A1 | 6/2016 | |

* cited by examiner

210

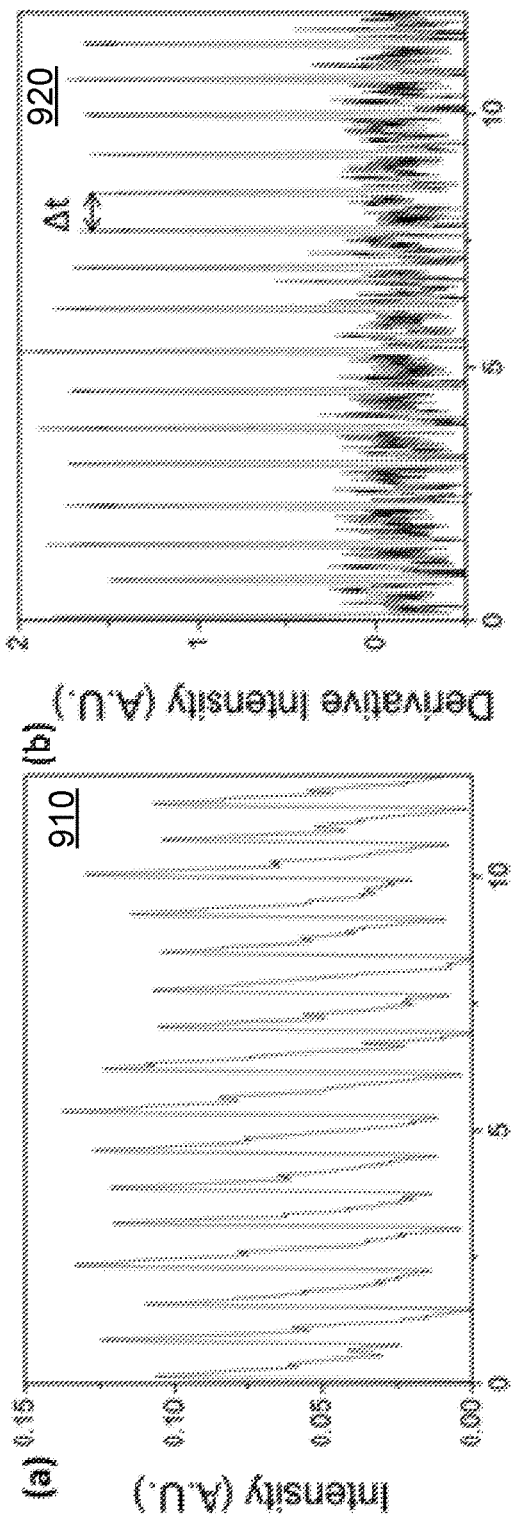
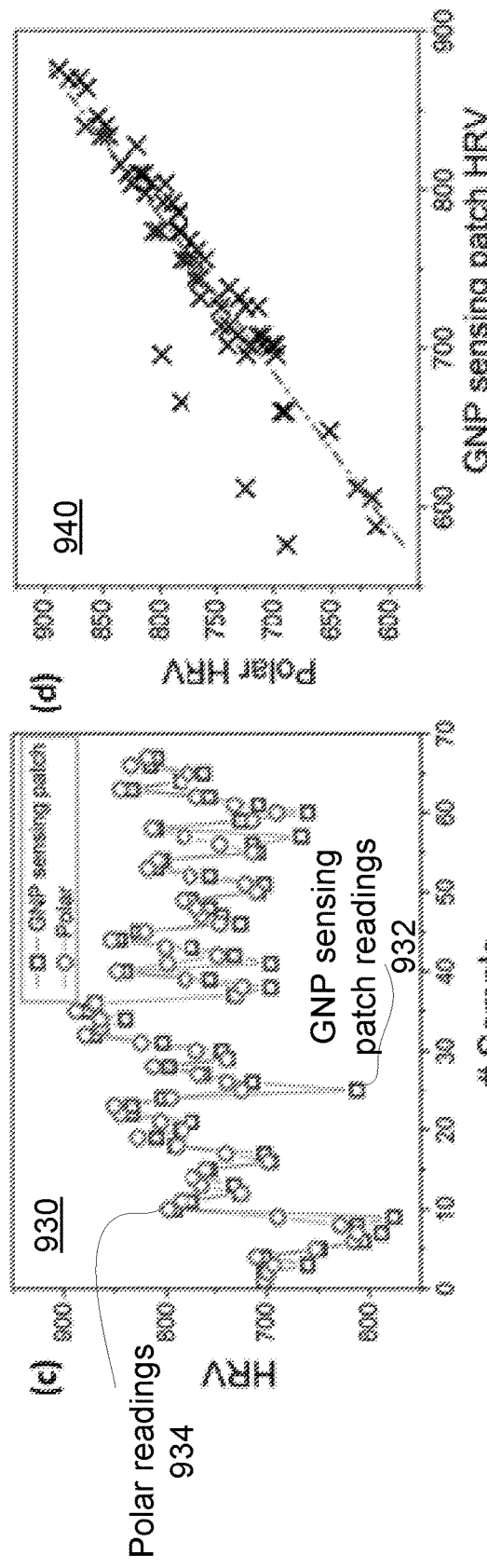
FIG. 9A
FIG. 9B
FIG. 9C
FIG. 9D

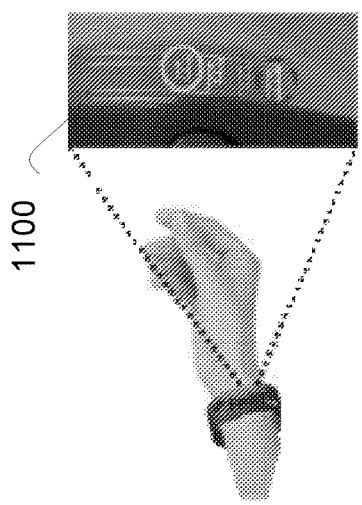
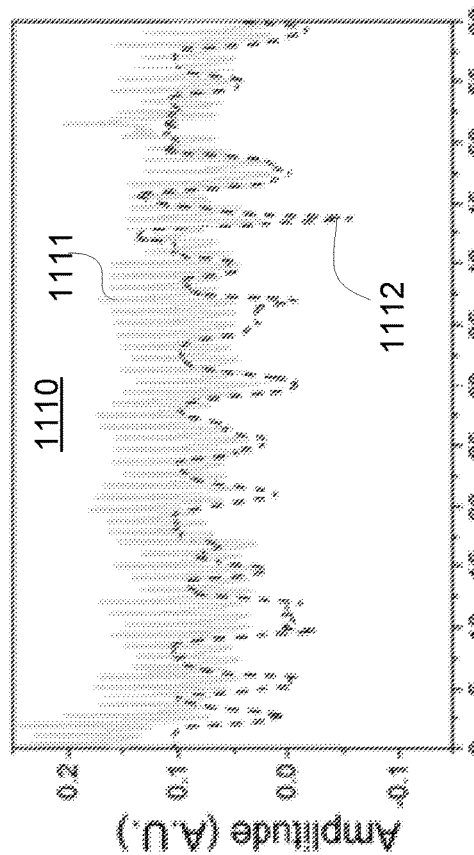
FIG. 11B
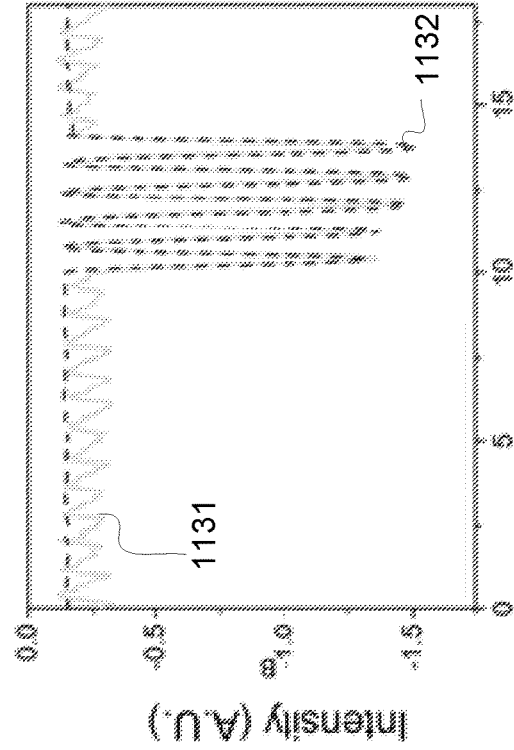
FIG. 11D
FIG. 11A
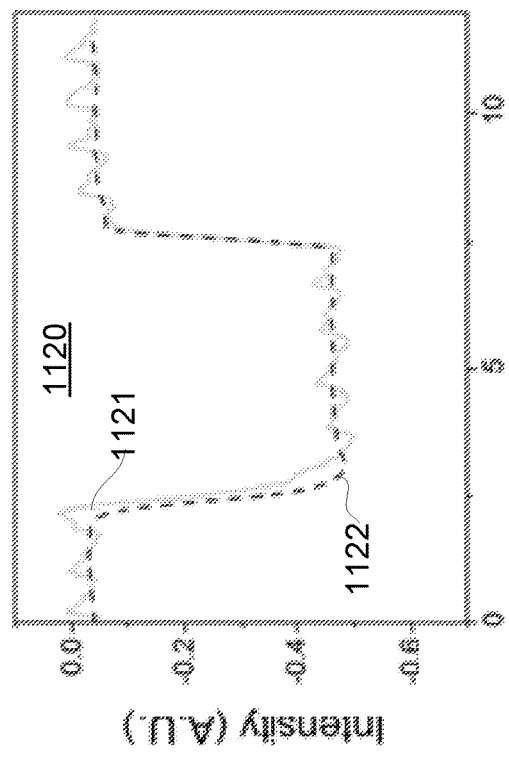
FIG. 11C

CARDIAC WAVEFORM SENSING

CROSS REFERENCE TO RELATED APPLICATIONS

This application claims the priority from U.S. provisional patent Ser No. 62/349,722 filing date Jun. 14, 2017 which is incorporated herein in its entirety.

BACKGROUND

There is a growing need to monitor cardiac waveforms—especially in an accurate and cost-effective manner.

SUMMARY

According to various embodiments of the invention there may be provided a pressure sensing device and/or a method for activating the pressure sensing device.

There may be provided a method for manufacturing a gold nanoparticles sensing element, the method may include printing a gold nanoparticle ink to form at least one sensing element; and photonic sintering of the at least one sensing element.

There may be provided a method for sensing, the method may include positioning, on one or more organs of living being, sensing elements that form an array of sensing elements and other sensing elements that form another array of other sensing elements; wherein the sensing elements are positioned at a first location; wherein the other sensing elements are positioned at second location that is spaced apart from the first location; wherein the sensing elements and the other sensing elements comprise one or more piezoresistive materials; wherein the sensing elements comprise a first sensing element; wherein the other sensing elements comprise another first sensing element; sensing, by at least one sensing circuit, a resistance of the first sensing element and a resistance of the first other sensing element; and determining a certain parameter of a cardiac waveform of the living being, by comparing between the resistance of the first sensing element and a resistance of the first other sensing element.

There may be provided a sensing device that may include sensing elements that elements comprise a first sensing element, a second sensing element; wherein each sensing element may include one or more piezoresistive materials; and a sensing circuit that is coupled to the sensing elements, wherein the sensing circuit is configured to sense a resistance of the first sensing element and of the second sensing element, and to determine, based on the resistance of the first sensing element and of the second sensing element, a first parameter of a cardiac waveform of a living being, wherein the cardiac waveform (a) is sensed by the first sensing element, and (ii) is sensed by the second sensing element.

There may be provided a sensing device that may include sensing elements that comprise a first sensing element, a second sensing element; wherein each sensing element may include one or more piezoresistive materials; and at least one sensing circuit that is coupled to the sensing elements, wherein the sensing circuit is configured to sense a resistance of the first sensing element and a resistance of the second sensing element, and to determine, based on the resistance of the first sensing element and the resistance of the second sensing element, a parameter of a cardiac waveform of a living being, based on the resistance of the first sensing element and on the resistance of the second sensing element; wherein the cardiac waveform (i) is sensed by the first sensing element, and (ii) is sensed by the second sensing element.

There may be provided a method, the method may include—positioning, on a person, sensing elements that comprise a first sensing element and a second sensing element; wherein each sensing element may include one or more piezoresistive materials; sensing, by a sensing circuit that is coupled to the sensing elements, a resistance of the first sensing element and of the second sensing element; and determining by the sensing circuit and based on the resistance of the first sensing element and of the second sensing element, a first parameter of a cardiac waveform of a living being, wherein the cardiac waveform (a) is sensed by the first sensing element, and (ii) is not sensed by the second sensing element.

There may be provided a sensing device that may include sensing elements that elements comprise a first sensing element, a second sensing element; wherein each sensing element may include one or more piezoresistive materials; and a sensing circuit that is coupled to the sensing elements, wherein the sensing circuit is configured to sense a resistance of the first sensing element and of the second sensing element, and to determine, based on the resistance of the first sensing element and of the second sensing element, a first parameter of a cardiac waveform of a living being, wherein the cardiac waveform (a) is sensed by the first sensing element, and (ii) is not sensed by the second sensing element.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIGS. 9A-9D illustrate waveforms according to an embodiment of the invention

FIGS. 11A-11D illustrate a sensing device and various waveforms according to an embodiment of the invention;

DETAILED DESCRIPTION OF THE DRAWINGS

Figure 1:
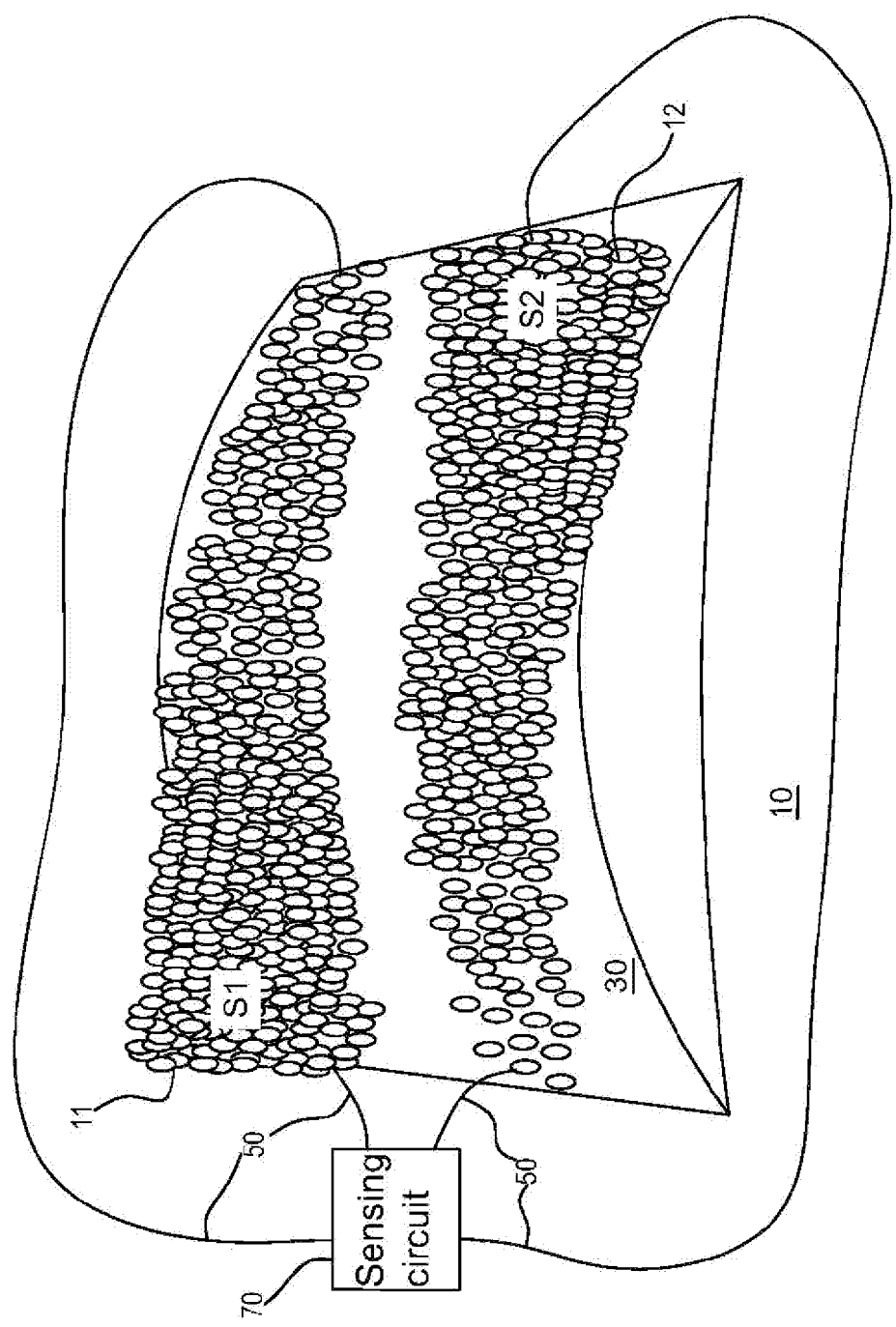
FIG. 1 illustrates a sensing device according to an embodiment of the invention.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

Because the illustrated embodiments of the present invention may for the most part, be implemented using electronic components and circuits known to those skilled in the art, details will not be explained in any greater extent than that considered necessary as illustrated above, for the understanding and appreciation of the underlying concepts of the present invention and in order not to obfuscate or distract from the teachings of the present invention.

Any reference in the specification to a method should be applied mutatis mutandis to a device capable of executing the method.

Any reference in the specification to a device should be applied mutatis mutandis to a method that may be executed by the device.

Non-limiting examples of a piezoresistive materials included in the first and/or second sensing elements include nanoparticles, carbon nanotubes and nanowires.

For brevity of explanation the following explanation refers to nanoparticles. Any reference to a nanoparticle should be applied mutatis mutandis to a reference to a piezoresistive material such as but not limited to carbon nanotubes or nanowire.

According to an embodiment of the invention there may be provided a sensing device for measuring a pulse waveform (cardiac waveform) without the use of conventional pulse oximetry devices (PPG via SpO2 sensors)—but rather by using highly sensitive nanotechnology based strain sensing elements (sensing elements) that monitor the arterial pulse pressure-wave.

The sensing device may be a wearable sensing device capable of coping with noise from body movements and ambient conditions.

The sensing device may be a wearable sensing device that would continuously (or non-continuously) monitor a pulse waveform of people (such as but not limited to people with high risk of cardiovascular related problems) and may improve the ability of healthcare providers to react quickly to life threatening deterioration in a person's clinical state.

The sensing device would also be attractive for fitness monitoring uses as well as mental health and stress monitoring.

The sensing device may include nanoparticles that may be shaped in various manners—such as with or without gradients. Non-limiting example of a gradient may include a thickness gradient, a width gradient, a concentration gradient, a resistance gradient, a sensitivity to strain gradient, a capping layer thickness gradient, a cross section gradient, and the like. Examples of sensing elements with gradients are shown in PCT patent application WO2016/092494 International Filing Date 9 Dec. 2015, which is incorporated herein by reference.

There is provided a sensing device that may include sensing elements that form a two-dimensional array of sensing elements. The sensing elements may include one or more piezoresistive materials such as but not limited to gold nanoparticles (GNP). A piezoresistive material changes its resistivity as a response to pressure or strain. Non-limiting examples of a piezoresistive materials included in the first and/or second sensing elements include nanoparticles, carbon nanotubes and nanowires.

For brevity of explanation the following explanation refers to nanoparticles. Any reference to a nanoparticle should be applied mutatis mutandis to a reference to a piezoresistive material such as but not limited to carbon nanotubes or nanowire.

The two-dimensional array may be shaped and sized so that when the sensing device is positioned on an artery, a first sensing element is located on the artery (or at least close enough) to sense the cardiac waveform—while a second sensing element is not located on the artery (or is distant enough) and does not sense the cardiac waveform. The cardiac waveform introduces minute pressure changes that are sensed by the first sensing element. In some embodiments, a distance between adjacent sensing elements exceeds 1 millimeter.

The length and a width of the two-dimensional array exceed 0.5 centimeters—which is slightly larger than a width of an artery.

The number of sensing elements may range between 2, 3, 100 and even more than 1000.

A non-limiting example of an array includes eight sensing elements that are arranged in two rows. Each row has four sensing elements in it with dimensions of 1×3 mm and spacing of 2 mm between the sensing elements in the same row. The spacing between the rows is 5 mm. The size of each sensing element can range from μm to several mm. The spacing between the sensing elements can range from μm to several mm the sensing elements in the array can be arranged as a long row, several rows, and a circle.

The two-dimensional array may be an ordered array, a non-ordered array, may include sensing elements that are positioned along a virtual curved line, may include sensing elements that are positioned along two lines that are oriented to each other, may include a grid of sensing elements, may include one or more rows of sensing elements and one or more columns of sensing elements, and the like.

Due the two-dimensional arrangement of the sensing elements the sensing device may be positioned at the vicinity of the artery—and at a lower accuracy than in the case of having a single sensing element.

The sensing device also includes a sensing circuit that is coupled to the sensing elements, wherein the sensing circuit is configured to sense a resistance of the first sensing element and of the second sensing element, and to determine a first parameter of a cardiac waveform of a living being.

By comparing between the resistance of the first sensing element and the resistance of second sensing element the sensing device may compensate for mechanical movements of the living being that is monitored—thus increasing the accuracy of the sensing process.

There may be provided a method for sensing, the method may include: (a) positioning, on an organ of a living being, sensing elements that form a two-dimensional array of sensing elements. The sensing elements may include one or more piezoresistive materials. The sensing elements may include a first sensing element and a second sensing element; (b) sensing, by a sensing circuit that is coupled to the sensing elements, a resistance of the first sensing element and of the second sensing element; (c) determining, by the sensing circuit, a first parameter of a cardiac waveform of a living being, wherein the cardiac waveform (i) is sensed by the first sensing element, and (ii) is not sensed by the second sensing element.

There may be provided a method for sensing, the method may include: (a) positioning, on one or more organs of living being, sensing elements that form an array of sensing elements and other sensing elements that form another array of other sensing elements. The sensing elements are positioned at a first location. The other sensing elements are positioned at second location that is spaced apart from the first location. The sensing elements and the other sensing elements include one or more piezoresistive materials. The sensing elements may include a first sensing element. The other sensing elements includes another first sensing element; (b) sensing, by at least one sensing circuit, a resistance of the first sensing element and a resistance of the first other sensing element; and (c) determining a certain parameter of a cardiac waveform of the living being, by comparing between the resistance of the first sensing element and a resistance of the first other sensing element. The resistance is measured at multiple points in time.

The certain parameter may be a pulse wave velocity.

The sensing elements may or may not form a two-dimensional array. The other sensing elements may or may not form a two-dimensional array.

The at least one sensing element may also take into account the resistivity of one or more sensing elements of the sensing elements and/or of the other sensing elements—that do not sense the cardiac waveform. This may include performing movement compensation.

The term pixel may refer to one or more sensing elements that are proximate to each other.

FIG. 1 illustrates a strip 10 that includes two gold nanoparticle strips (GSSs) 11 and 12 that are spaced apart from each other and mounted on a flexible substrate 30 according to an embodiment of the invention.

Both GSSs have a triangular shape with opposite slopes—wherein in one GSS the rightmost edge is of a maximal height and in another GSS the leftmost edge of maximal height.

It is noted that the cross section of the GSS may change at another manner (for example the width of the GSS can change in an anti-symmetric manner—as illustrated in FIG. 1, and/or a combination of both height and width may change). FIG. 1 also shows conductors 50 and sensing circuit 70. Sensing circuit 70 measures the resistance of the first and second GSSs 11 and 12.

It is noted that the number of conductors 50 may equal four or may differ from four. For example, one conductor may be connected in parallel to one end of each one of GSSs 11 and 12. It is noted that sensing the resistance is equivalent to sensing the conductivity of the GSSs or any sensing of any electrical and/or magnetic parameter of the sensing element that is indicative of the occurrence of the event.

The sensing circuit may be included in the strip or may be coupled to the strip. The sensing circuit 70 may be configured to measure the resistance by any known method. The sensing circuit 70 may be in proximity to the GSSs, or located in a greater distance. It may be a part of a flexible patch or coupled to the patch.

The GSSs may be produced by any applicable method. For example, they may be manufactured by a "propelled anti-pinning ink droplet (PAPID)" manufacturing process which is suitable for fabrication of centimeters long GNP lines.

Using the PAPID approach, two 8 mm long GNP sensing strips (2-GSS) with countero.5-directional thickness gradients and resistance of ~50 MΩ were fabricated over a strip of polyimide foil. The cross-sectional thickness gradients and related morphology were studied and verified using High Resolution Scanning Electron Microscopy.

According to an embodiment of the invention the GSSs and/or the strip itself may be protected by a protective layer that may be connected to the GSSs and/or the strip. The protective layer may be thin enough such as not to isolate the GSSs and/or the strip from pressure and may be flexible. The protective layer may be connected to the GSSs and/or strip at an external facet (directed to the location from which pressure is expected to be applied) and/or to an internal facet.

A non-limiting example of a manufacturing process of the sensor may include Gold nanoparticles (GNPs) ink synthesis.

Gold(III) chloride trihydrate ($HAuCl_4.3H_2O$), tetraoctylammonium bromide (TOAB), sodium borohydride, and Hexanethiol were purchased from Sigma-Aldrich. A solution of $HAuCl_4$ was added to a stirred solution of TOAB in toluene. After stirring 10 min, the lower aqueous phase was removed. Organic ligands and sodium borohydride were subsequently added to the toluene phase. After 3 hours at ice temperature, the lower aqueous phase was removed and the toluene phase was subsequently evaporated by rotary evaporation. After first washing with cold ethanol, the solution was kept at 5° C. for 18 h until achieving complete precipitation. The dark-brown precipitate was filtered off and washed with ethanol. The procedure was repeated three times to remove all leftover ions such as TOAB.

Printing Flexible, Skin Attachable Pulse and Movement Sensors

Following the GNPs ink synthesis, the "pulse patch" is fabricated using inkjet printer. Silver conductive ink (commercial) are printed first on a flexible substrate and then the GNP ink is being printed as the sensing layer. Several annealing processes are induced to enhance the sensor sensitivity towards small strains in the range that are generated by the human pulse. The "pulse patch" is then covered with a biocompatible protection layer (e.g., Polydimethylsiloxane). The "pulse patch" is connected to a custom made printed circuit board (PCB) as the electric circuit. This PCB can also contain a Bluetooth connection.

This prototype is tested for pulse waveform sensing while been exposed to different types of noises.

The sensor may apply various signal processing algorithms such as but not limited to mapping noises type and their effect on the developed "pulse patch" sensor.

The effect of different body movement on the "pulse patch" is been measured both in lab conditions and outdoors. The movements can be categorized by cyclic movement (e.g., typing on a keyboard or clicking on the phone) and by random movements (e.g., raising a hand). The responses of the "pulse patch" to those movements are been recorded during pulse monitoring so initial noise reduction and filtering algorithm can be developed.

Figure 2A:
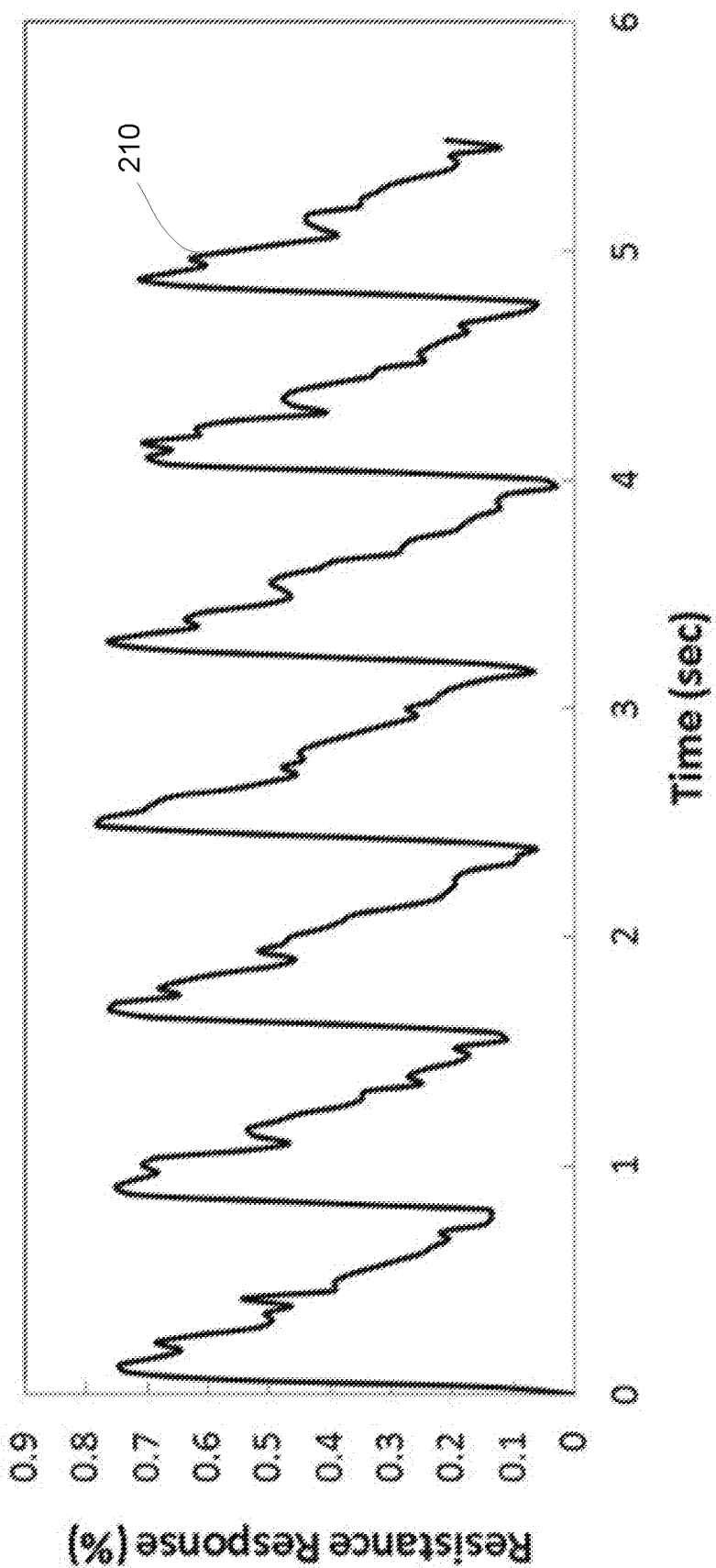
FIG. 2A illustrates waveforms according to an embodiment of the invention.

Curve 210 of FIG. 2A illustrates a resistance response over time of the prototype.

Figure 2B:
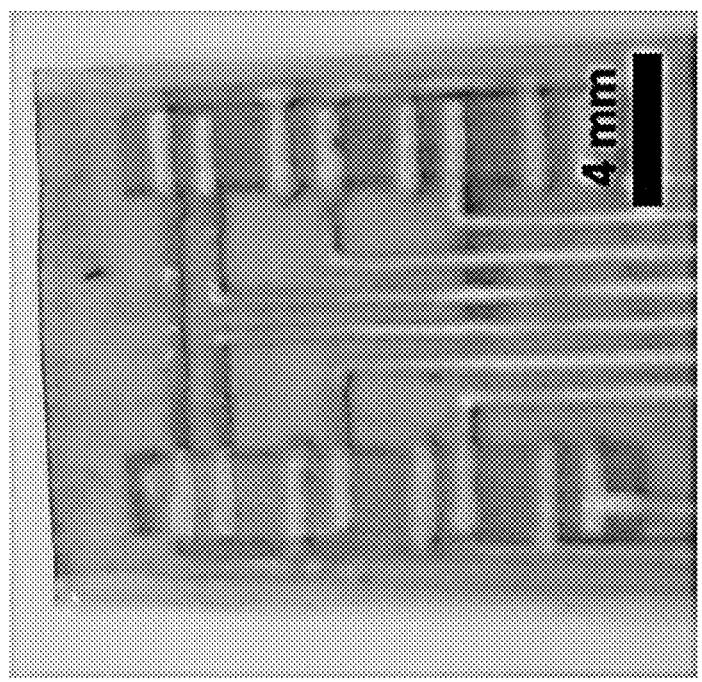
FIG. 2B illustrates sensing elements according to an embodiment of the invention.

FIG. 2B includes an image 210 of the prototype of such "pulse patch" and the related electronic board.

The sensor may be a flexible pulse-waveform monitoring patch based on piezoresistive nanoparticle films (in short—pulse piezo sensor). The device is composed of a flexible substrate, conductive electrodes and a strain sensitive sensing film based on gold nanoparticles. The conductive electrodes and the sensing layer could be printed using conventional printed electronics techniques (e.g., inkjet printing, screen printing, pad printing and more) on the flexible substrate.

The sensing elements are comprised of several local point strain sensors (strain sensing pixels). Optimally, one or few strain sensing pixels are adhered to the skin adjacent to an artery, enabling them to record the pulse waveform through the strain inflicted by the pulsating artery (FIG. 2A). Additional sensing pixel/pixels will be adhered to the skin in proximity to the pulse sensing pixels, but not placed over the artery rather next to it, so they will not be subjected to strain inflicted by the pulsating artery. Those sensing pixels will be used as reference sensors for environmental and mechanical noise monitoring and calibration.

Figure 3:
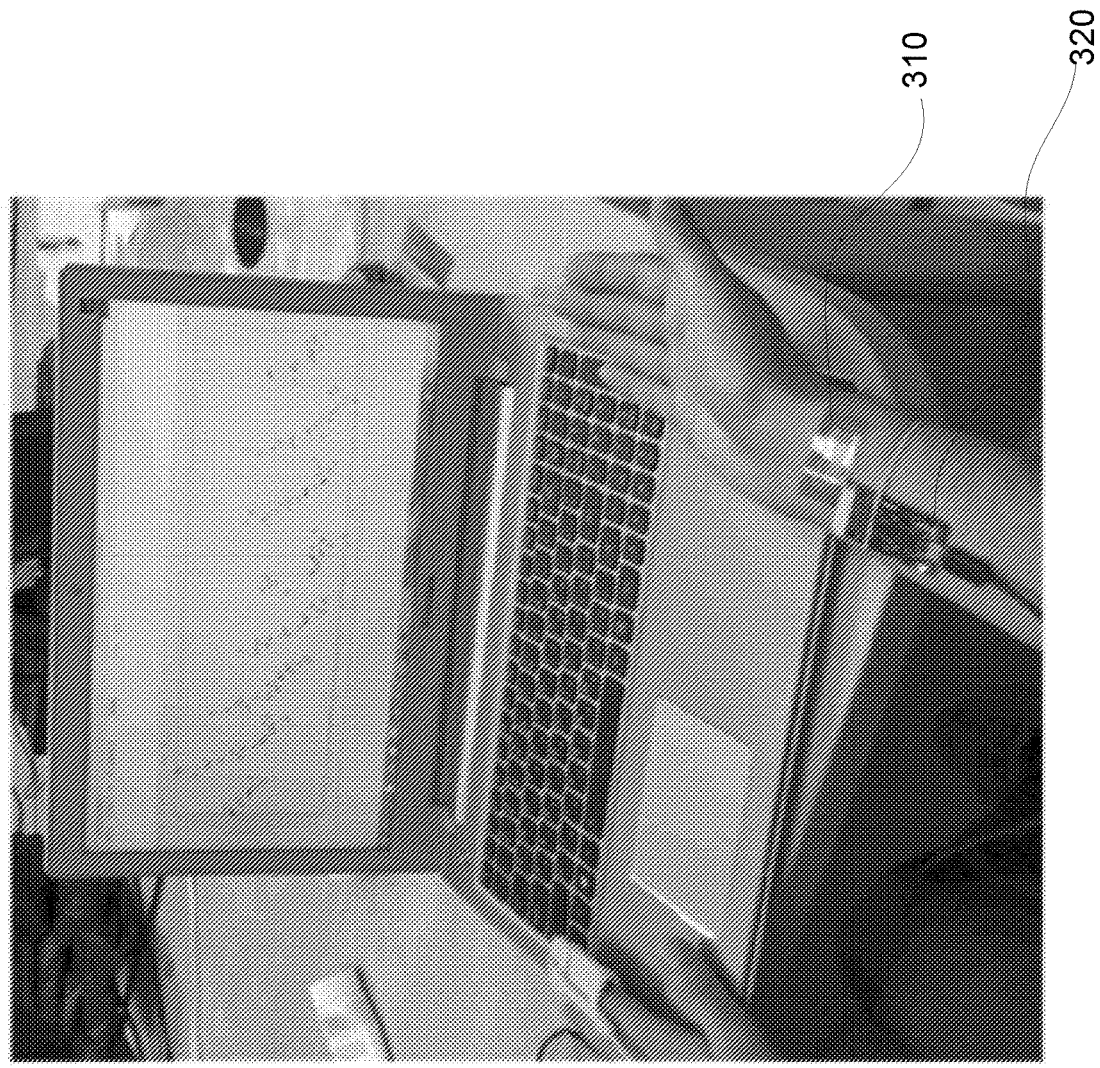
FIG. 3 illustrates a setup according to an embodiment of the invention.
Figure 4:
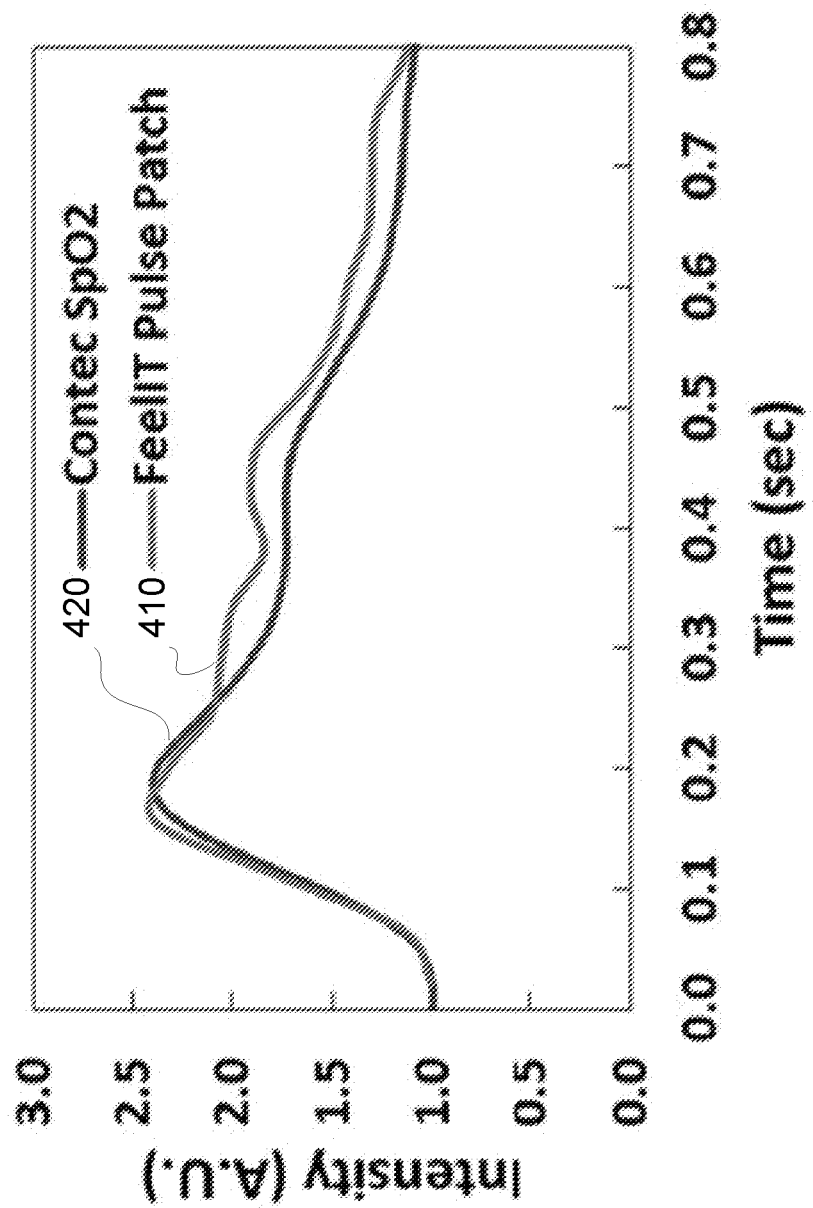
FIG. 4 illustrates waveforms according to an embodiment of the invention.

The pulse piezo sensor was compared to a commercial pulse oximeter that is worn on the finger (company: Contec). The experimental setup is presented in FIG. 3—sensing element array 310 and sensing circuit 320. The average of the first 30 pulse waveforms (waveform of the FeelIT pulse patch 410 and waveform of the Contect SPo2 sensor 420) is depicted in FIG. 4. Both pulse sensors have similar peaks. The waveform obtained from the pulse piezo sensor consists of additional peaks which can be attributed to some noises or it may contain some additional data.

Figure 5:
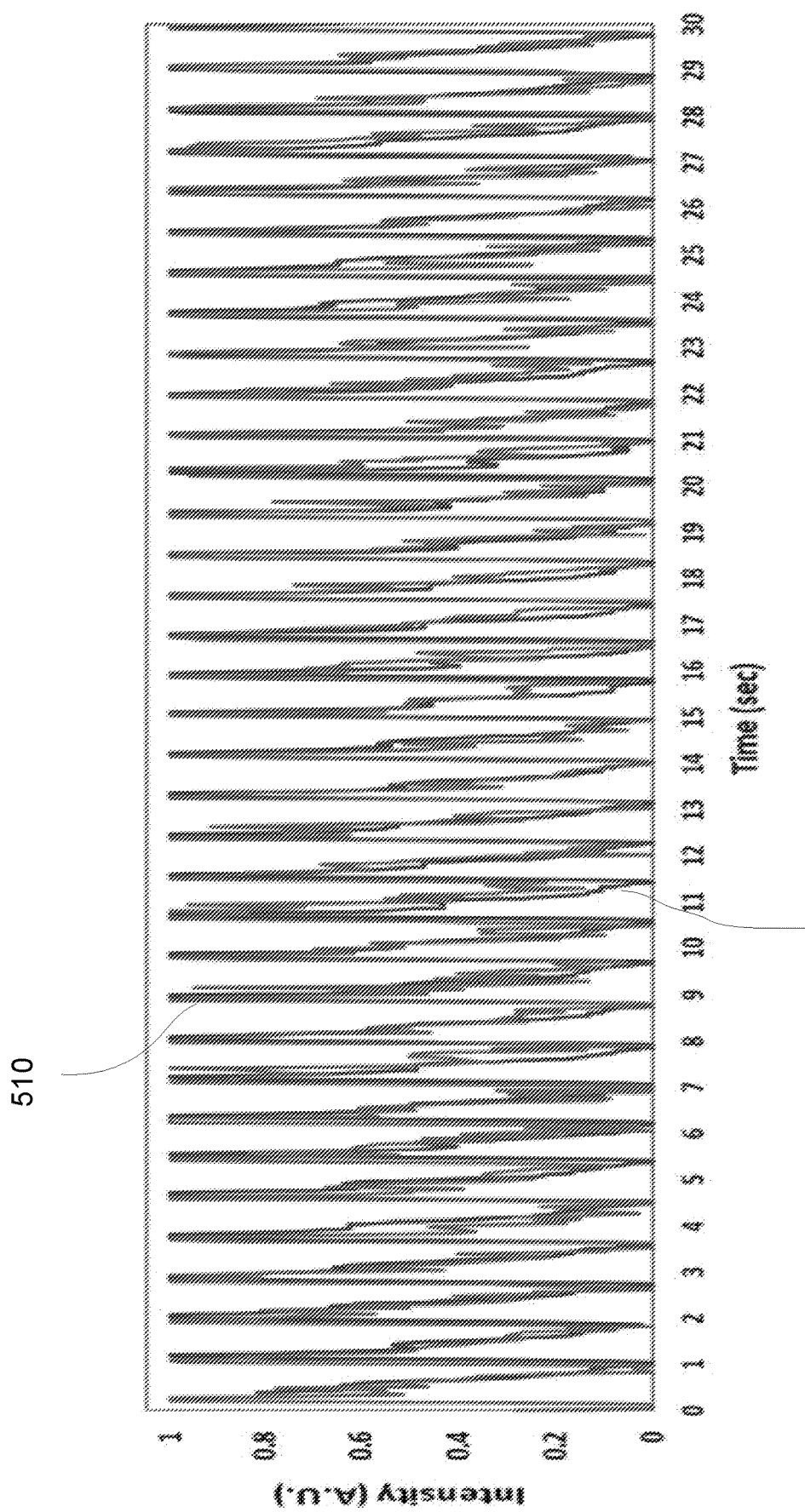
FIG. 5 illustrates waveforms according to an embodiment of the invention.

The pulse waveform of 30 seconds measurement shows a good correlation between the two types of pulse sensors (see FIG. 5). In FIG. 5—waveform of the FeelIT pulse patch 510 and waveform of the Contect SPo2 sensor 520.

It should be noted that the data presented for the pulse piezo sensor is the raw data and no filtering was done apart from low pass filtering by subtraction of the lowest frequency from the original waveform as well as normalization to the baseline resistance.

Noise identification and handling is a challenge for pulse oximetry devices. This challenge is critical for application that requires long time monitoring or pulse monitoring during physical activity. The main way to treat this issue is by filtering movement's related noise in the software level. Those tools are least effective if the movement has a periodical nature, in which case the movement signal can be misread as the pulse signal (especially for periodical movements that have a similar frequency as the pulse, such as typing, walking, or running) The effect of finger movement on the pulse oximetry sensor signal is presented in FIG. 6A.

Figure 6A:
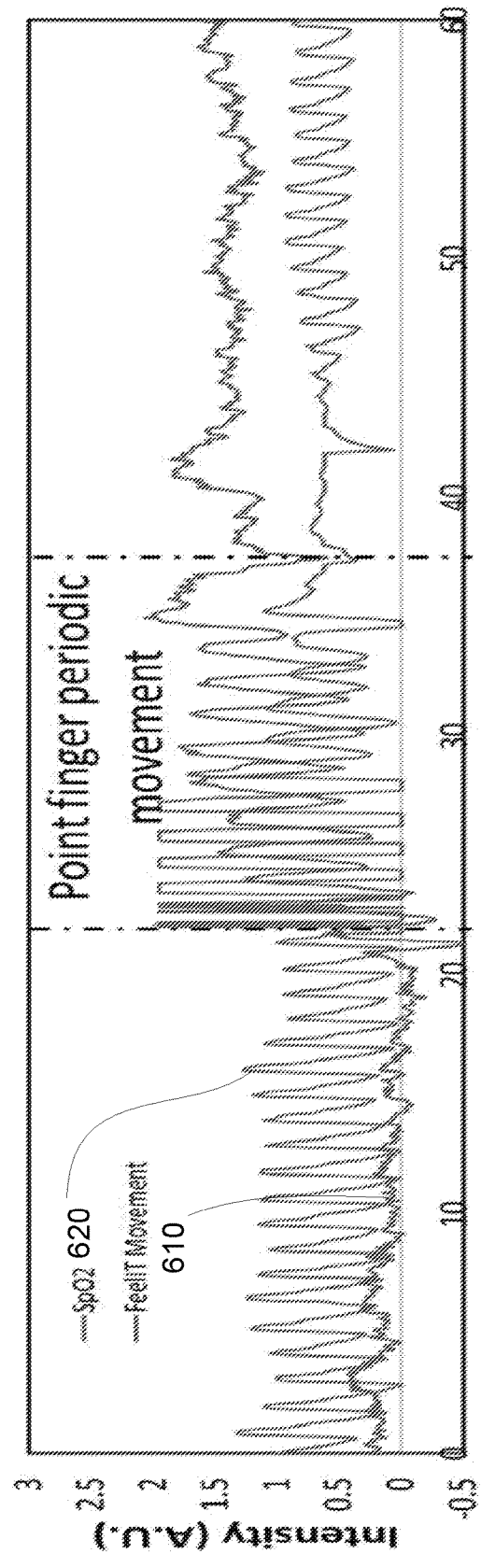
FIGS. 6A-6B illustrate waveforms according to an embodiment of the invention.
Figure 6B:
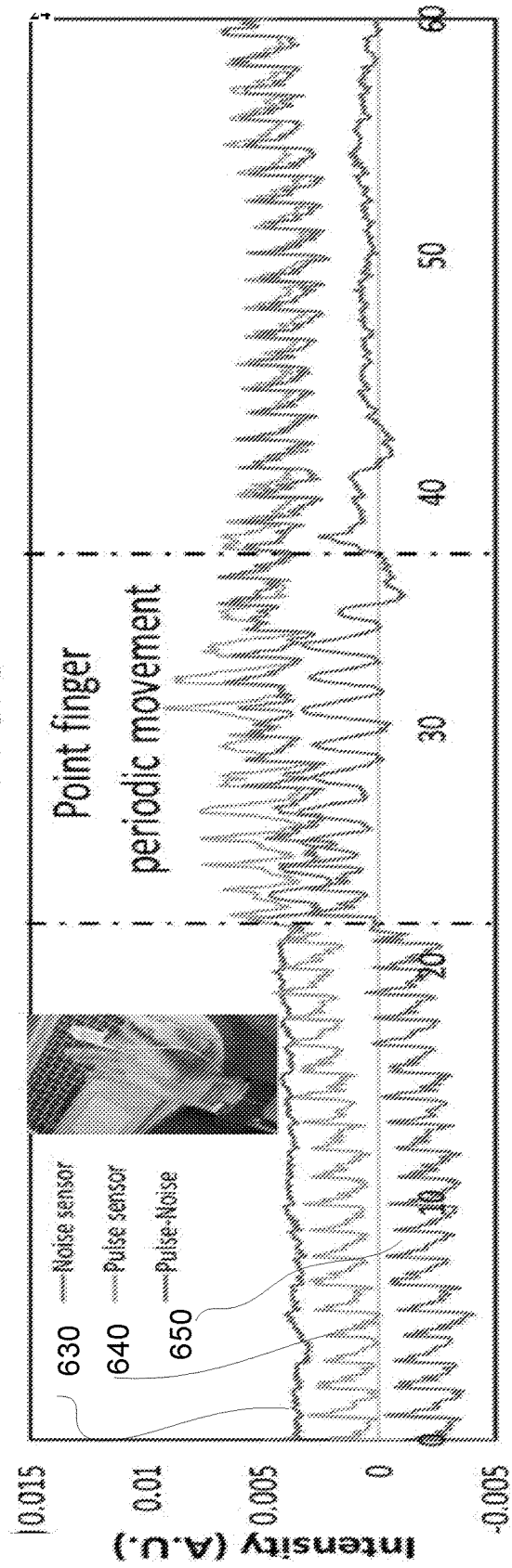

In FIG. 6A—Finger cuff PPG (from Contec) signal while subjected to finger periodical movement (620) movement sensing signal from movement sensor in the GNP sensing patch (610). In FIG. 6B—the movement related noise reduction using pulse sensitive pixels (640) and movement sensitive pixel (630) on the same sensing platform yielding an improved pulse signal (650).

In the pulse piezo sensor, the additional sensing pixel/pixels that were adhered to the skin in proximity to the pulse sensing pixels sense movements and can be used as reference sensors.

The integration of several sensing pixels on the same platform can yield an improved noise cancellation setup since a reference signal can be obtained for the reference sensors and can be used for additional mathematical manipulation for movement related noises reduction (FIG. 6B).

The device could be located at different sited on the body. For example: on the wrist at the base of the palm, on the chest, on the neck. At specific body locations (e.g., the chest) additional vital signs can be monitored (e.g., breathing rate).

The device could be adhered to the skin or it could be held on the body while applying a range of pressures.

The next generation of such sensors will allow monitoring additional physiological parameters like body temperature and dehydration while considering environmental effects such as temperature and humidity. Another aspect is wireless communication and power consumption. The developed technology has low power consumption and therefore enables operation of the devise for a few days with a small "coin" battery.

Applications for the sensor may include (for example only) monitoring pulse and hemodynamic parameters for patients admitted to hospitals; people suffering from chronic cardiovascular problems (home healthcare monitoring); athletes during physical activity; newborn babies at risk; people engaged in sports activities; eastern medicine diagnosis and treatment monitoring; Mental conditions (stress, excitement depression etc.)

The sensor may measure the pulse waveform with sensing layer of gold nanoparticles, may perform calibration of body movement related noise with neighboring reference sensors, may perform Identification of events of mechanical movements of the skin that inflict noise to pulse waveform readings by strain sensors of pulse oximetry (SpO2) based device Conventional PPG sensors are commonly worn on the fingers. However, this prior art configuration is not well suited to pervasive sensing, as most daily activities involve the use of the fingers. The suggested sensor may be designed as a patch that could be adhered to the body at locations, such as the base of the palm, neck, or chest, which are more convenient and less restricting than on the finger or the ear.

Wristwatch-type pulse oximetry and blood pressure sensors have been developed and commercialized by several companies. These devices, although much easier to wear, are not usually used in clinical settings, due to several technical issues. The constant moving of the hand might bring a lot of noise to the waveform measurement.

The suggested sensor has few improvements over wristwatch-type pulse oximetry sensors: (i) the configuration of the patch will enable more accurate pulse waveform readings and eliminate noise related to body, fingers, and wrist movements (which might affect wristwatch-type pulse oximetry sensors) (ii) the technology is based on strain sensing rather than wavelength absorption detection. Strain sensing is not sensitive to the optical absorbance of other tissues in the body and neither to external environmental light effects. (iii) The presence of neighboring reference strain sensing pixels enables calibration of noise related to body movements. (iv) the strain sensors can identify the occurrence of events of mechanical movements of the skin that inflict noise to pulse waveform readings by strain sensors of pulse oximetry (SpO2) based devices.

GNP Sensing Patch

Highly sensitive strain sensor based on GNP sensing layer was fabricated by printing GNPs based ink with toluene as solvent (see experimental). The GNP ink was printed on a thin Kapton substrate (25 μm). The sensing mechanism is based on tunneling mechanism whereas, the electrical resistance, R, of GNPs film as given in $$R = R_0 \exp(\beta l) \cdot \exp\left(\frac{E_a}{k_B T}\right)$$

the following equations:

where $\beta$ is the tunneling constant, l is the interparticle distance, $E_a$ is the activation energy (the energy barrier associated with charging adjacent metal cores), $k_B T$ is the characteristic thermal energy.

Figure 7A:
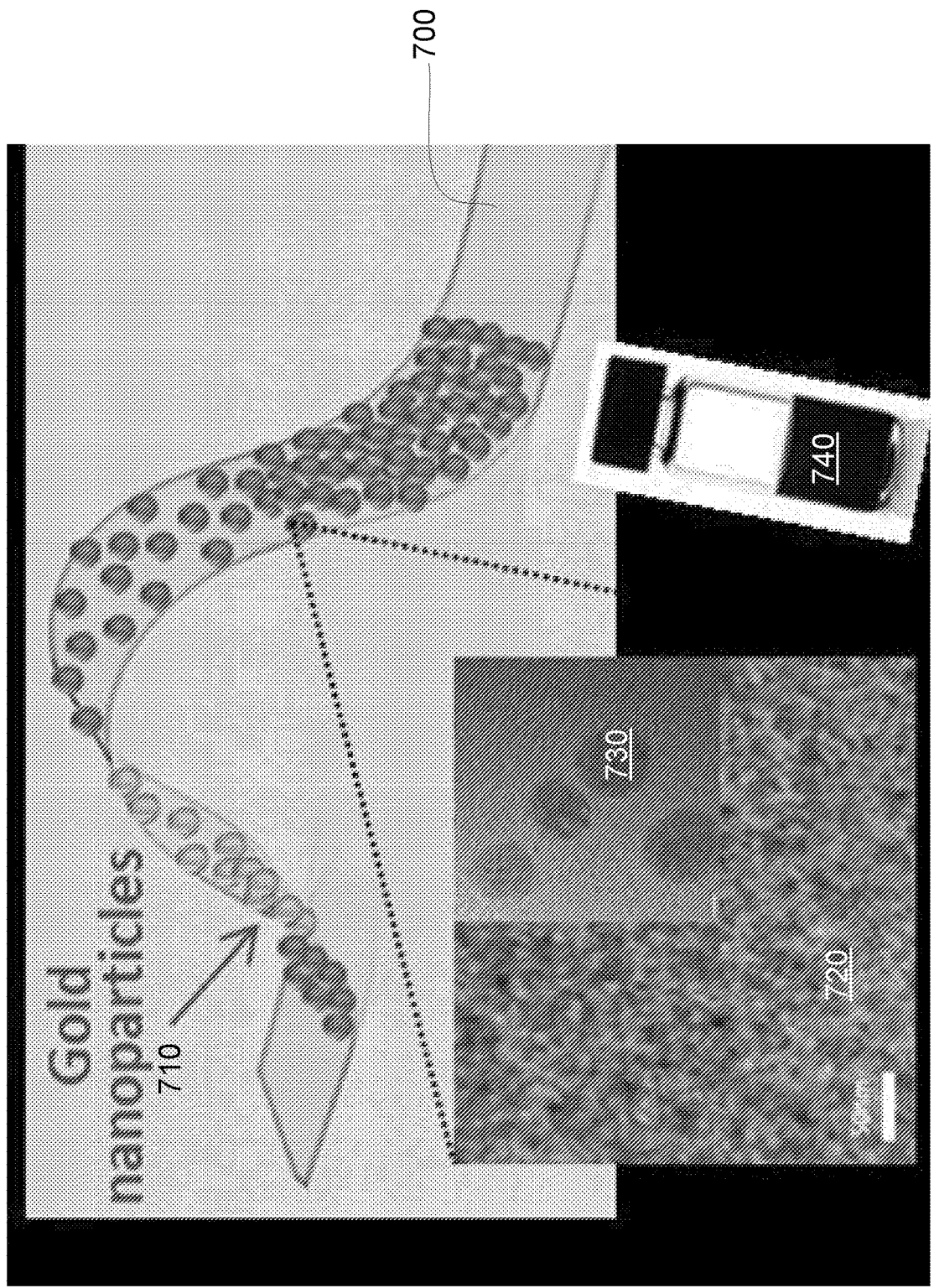
FIG. 7A illustrates sensing elements according to an embodiment of the invention.

FIG. 7A schematic illustrates the sensing mechanism to strain. When the GNP sensing layer ("gold particles 710) is printed on the upper part of the substrate 700, during bending the sensing layer will undergo stretching strain that will increase the interparticle distance, l, and therefore the resistance of the sensing layer will increase. The sensitivity to strain (e.g., the gauge factor) is defined as the ratio between the relative change is resistance upon strain. The characteristic gauge factor value for GNP sensing patch is ~200. FIG. 7A also include two magnified images of the GNP 720 and 730. FIG. 7A also illustrates a solution 740 of GNP ink.

Figure 7B:
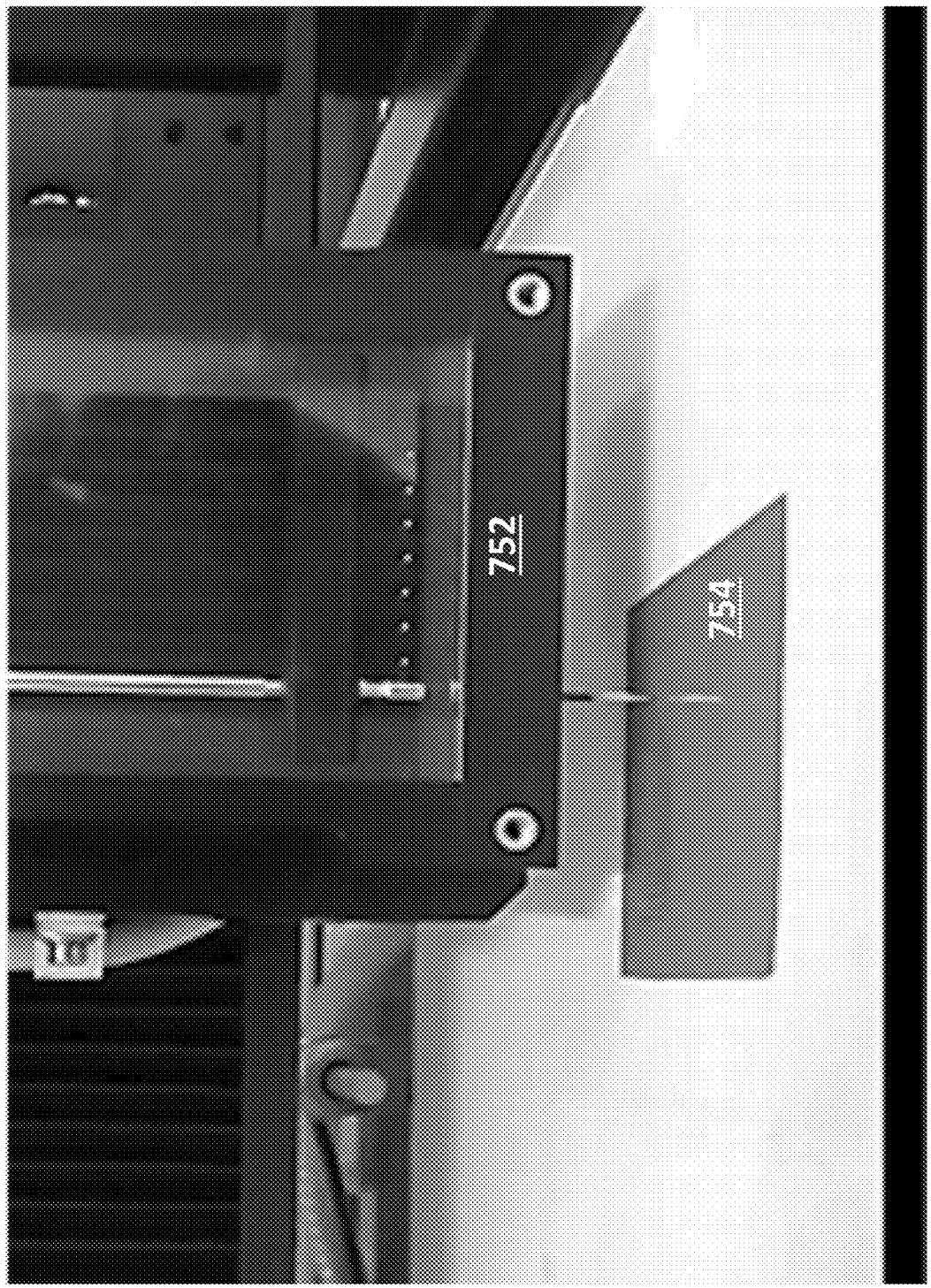
FIG. 7B illustrates a printer for printing the sensing elements according to an embodiment of the invention.

To achieve uniform and highly producible GNP sensing patches, sciFLEXARRAYER S3 printer (from: Scienion) 752 was used to print an array of sensors 754 (with dimensions of 1×3 mm each) as presented in FIG. 7B.

Figure 7C:
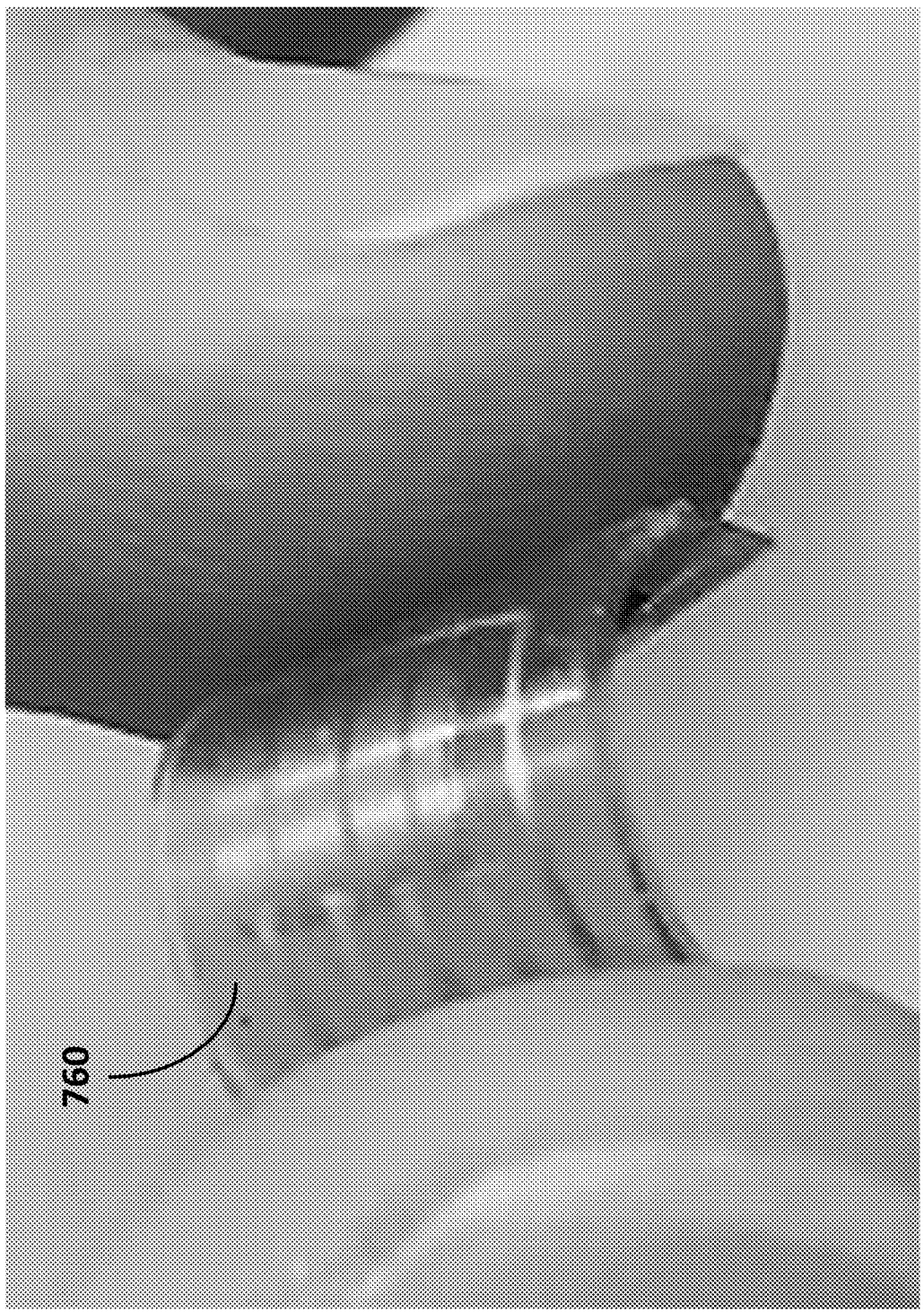
FIG. 7C illustrates sensing elements according to an embodiment of the invention.

Optic picture of the GNP sensing patch 760 is presented in FIG. 7C. This image illustrates the high flexibility of the patch. The sensing patch had 8 sensors in a 4×2 matrix design (see experimental). 10 GNP sensing patches were fabricated with a total of 80 sensors. The baseline resistance of all sensors was 21 MΩ±2.3 MΩ. Post processing treatment was done to enhance the sensitivity to strain and lower the resistance to values in the range of 200-500 KΩ as detailed in the experimental section.

The GNP sensing patch was adhered to the skin using an EEG paste (from D.O. Weaver and Co) and fixed to the wrist with a wristband 772 while the PCB board 774 with the related electronics was integrated in the wristband (see FIG. 7D—upper right side).

Figure 7D:
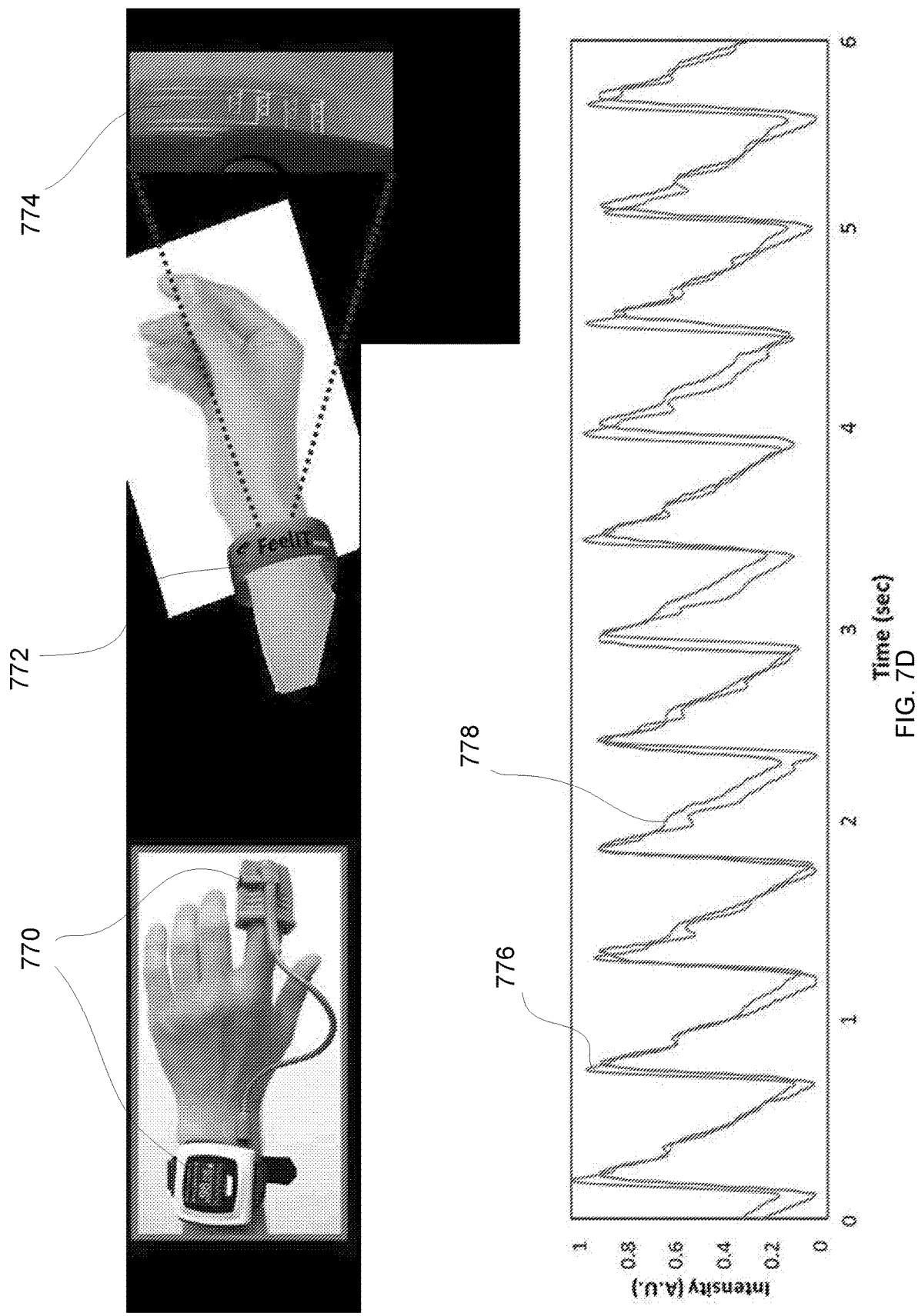
FIG. 7D illustrates a finger cuff PPG sensor and a sensing device according to an embodiment of the invention.

A finger cuff pulse oximeter from Contec (cms50f) 770 which is FDA approved was assembled on the index finger of the same hand for comparison (see FIG. 7D—upper left side).

The results are depicted in FIG. 7D—lower part. As can be seen, the two signals (778, 776) obtained from these two sensors (770 and 774—respectively) are very similar and the signal from the GNP sensing patch display clear and repetitive features in each waveform.

Using an array of GNP based sensors provides various benefits:
a. (i) locating the sensors on the artery is of high importance to get an accurate signal. By using an array of sensors, statistically, there is a good chance that one of the sensors will be located on the artery and therefore will give a good pulse waveform signal.
b. (ii) Movements reduction: while one (or more) sensor is located on the artery the others are located nearby and can be used as reference sensors.
c. (iii) There are some biometric features that can be extracted by measuring the pulse waveform with two or more sensors that are separated. One example for this is the pulse wave velocity (PWV).

The intensity of the response is depended on the location of the sensor on the artery and on the anatomy of the artery in the human body which may differ from person to person. We found that on the wrist, (the radial artery) the response to the pulse can generate responses of 0.1-1%. Resistance response of all the sensors is calculated as the percent change in resistance R with respect to the baseline resistance $R_b$ of the sensor ($\Delta R/R_b$). Therefore, we did not directly measure the pressure produced by the pulse wave. For measuring the pulse wave pressure, a model that reflects the artery autonomy and variation from person to person should be considered.

Biometric Data Collected from the Pulse Waveform

Figure 8A:
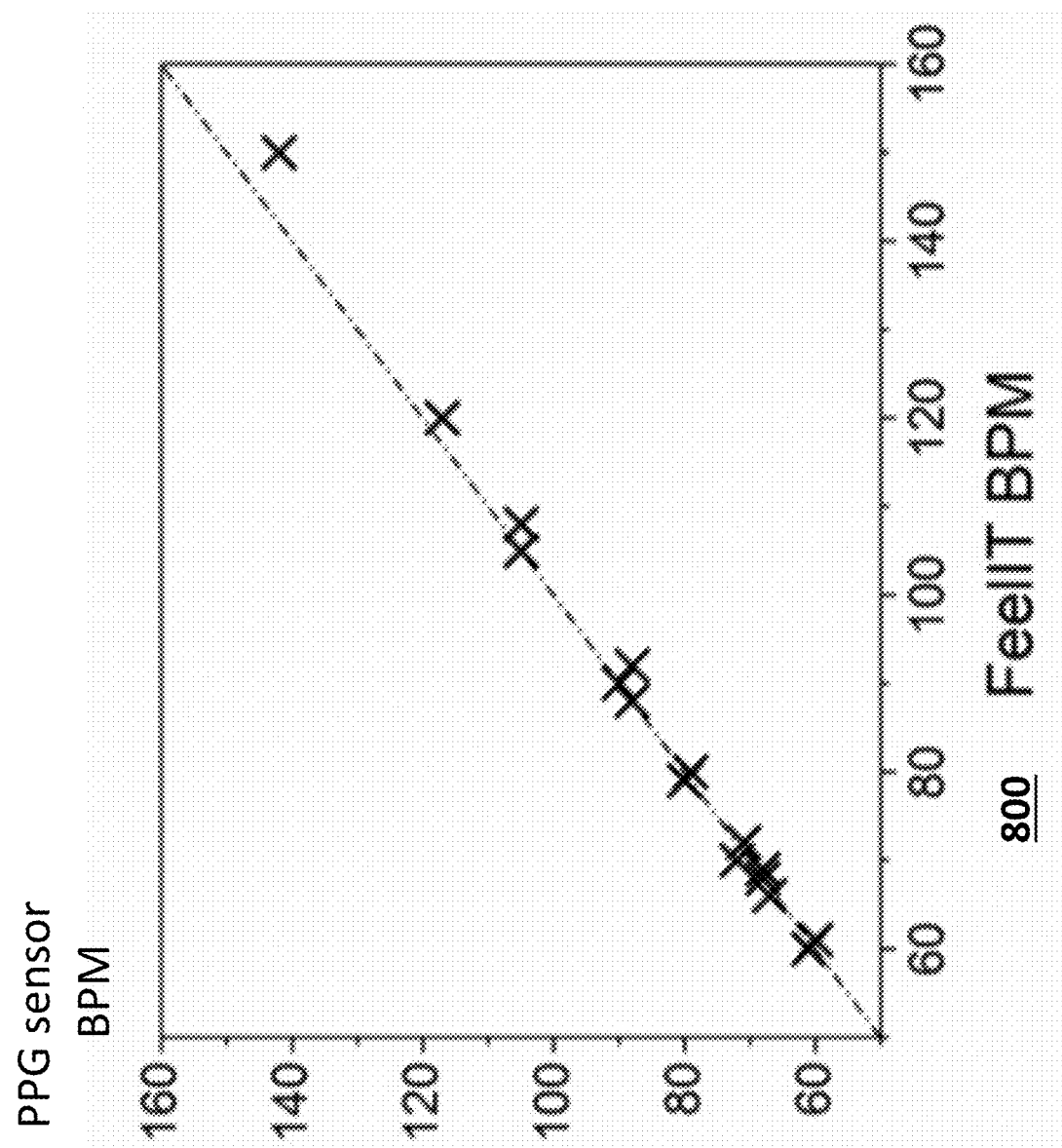
FIGS. 8A-8E illustrate waveforms according to an embodiment of the invention.

The pulse waveform can be analyzed and meaningful biometric data can be collected. The pulse waveform was recorded and analyzed by the GNP sensing patches from different subject. The results are presented in FIGS. 8a-8e. The most common feature that can be extracted from the waveform is the heart rate or beats per minutes (BPM). Similar algorithm was applied on waveforms that from a PPG sensor and from the GNP sensing patch for heart rate calculation. FIG. 8A (graph 800) shows high correlation between the measurements.

Figure 8B:
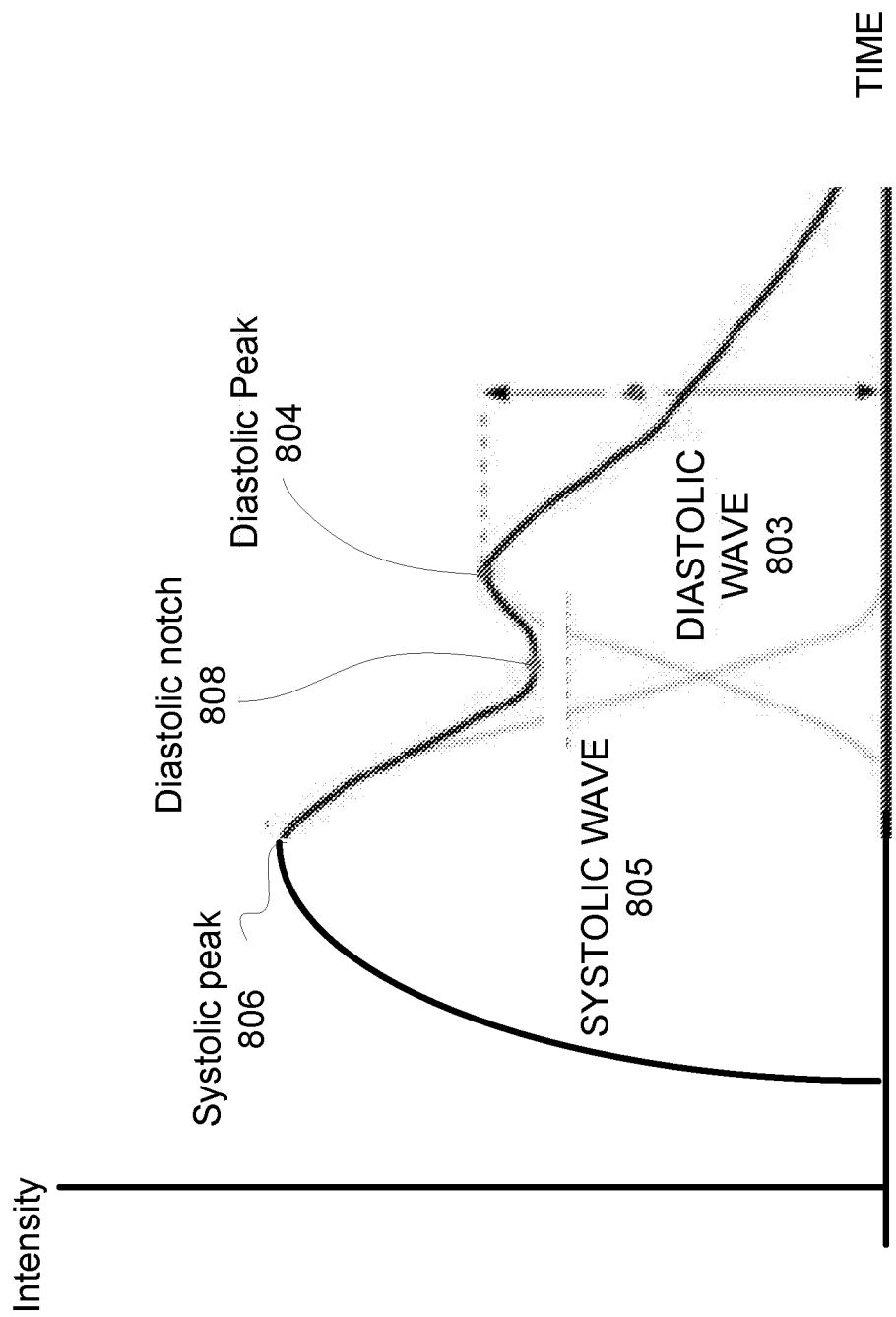
Figure 8C:
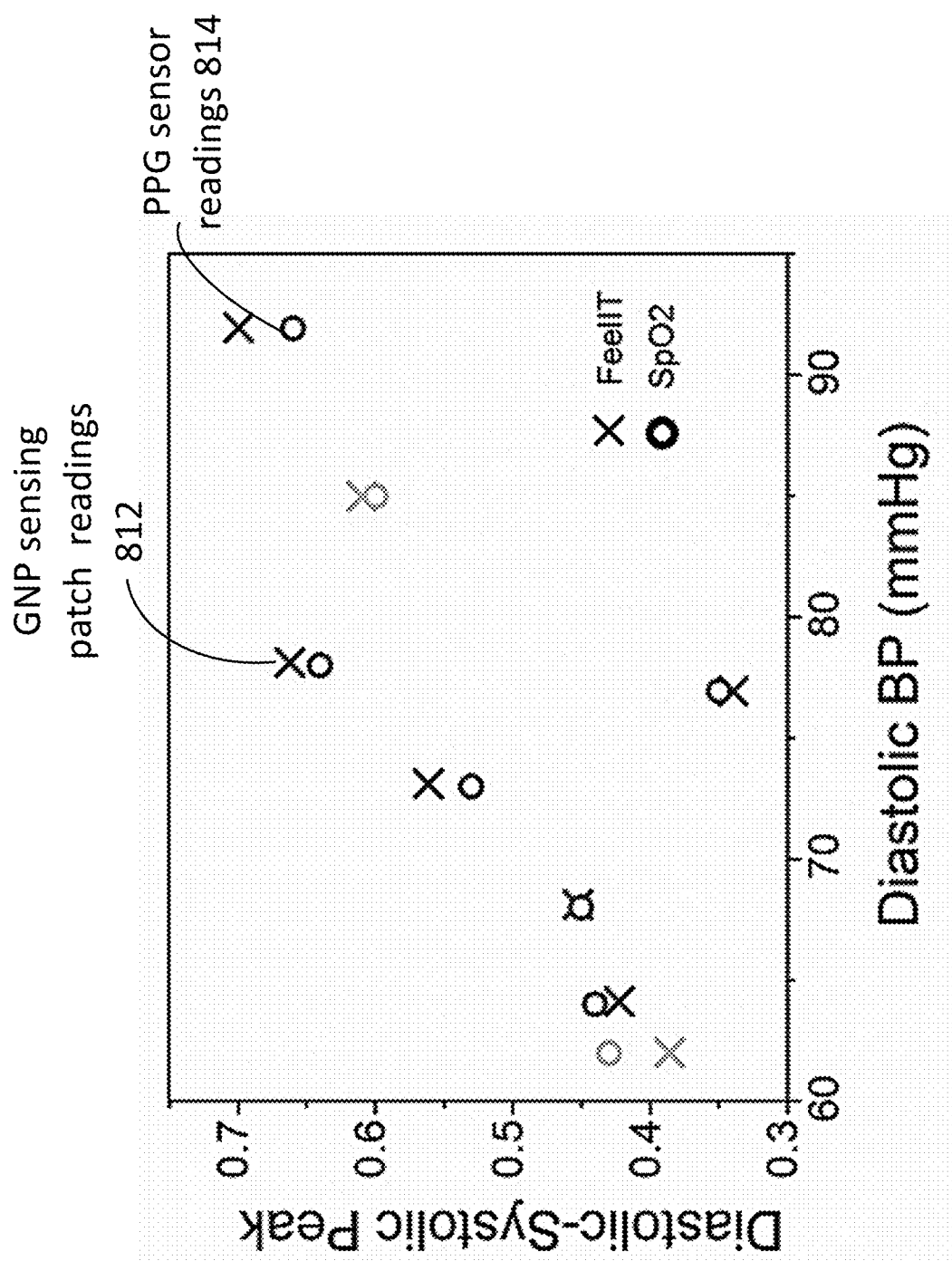

The waveform contour is displayed in FIG. 8B is a combination of systolic waveform 805 and diastolic wave 803—and includes indications of its main features such as the systolic peak 806, diastolic peak 804, diastolic notch 808. These features are indication of additional important biometric data such as changes in the diastolic blood pressure (BP). FIG. 8C presents the values of the systolic—the diastolic peaks as a function of the diastolic BP as was measured by arm cuff blood pressure monitor (from Rossmax). There were three different persons. There is a high correlation to the diastolic BP and a good match between the values that were obtained by the PPG sensor (readings denoted by "o" 814) and the GNP sensing patch (readings denoted by "x" 812). It should be noted the heart rate showed no correlation to the BP. The results may pave the way towards the development of a wearable cuff-less blood pressure monitoring device. By remotely measuring the BP (or even changes in the BP), the blood pressure variability (BPV) could be measured, which is considered a novel risk factor for cardiovascular disease.

Figure 8D:
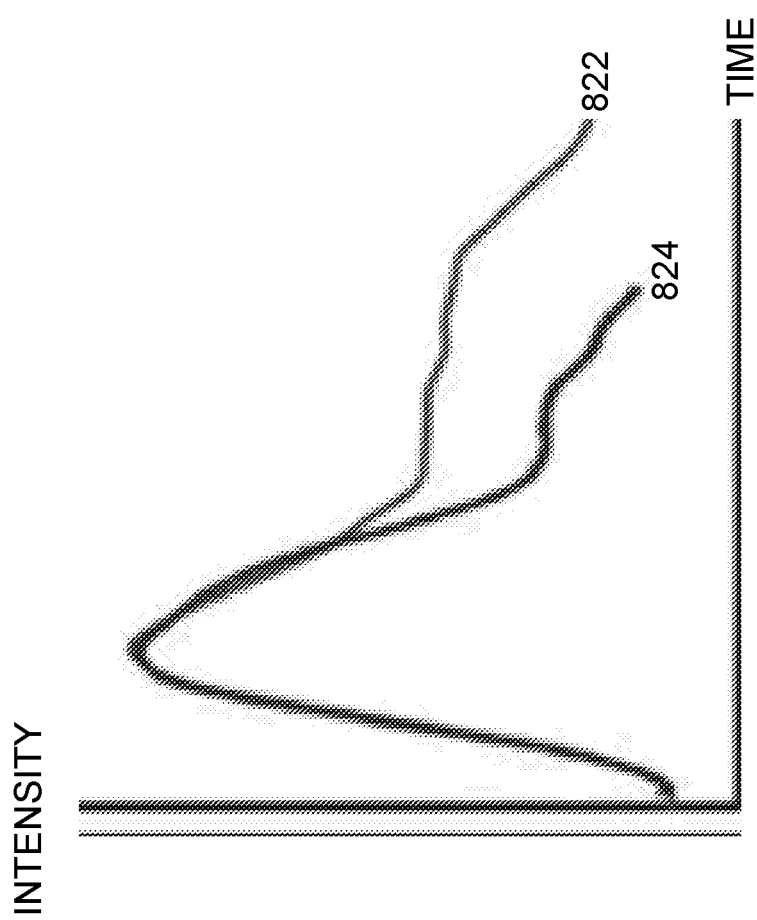
Figure 8E:
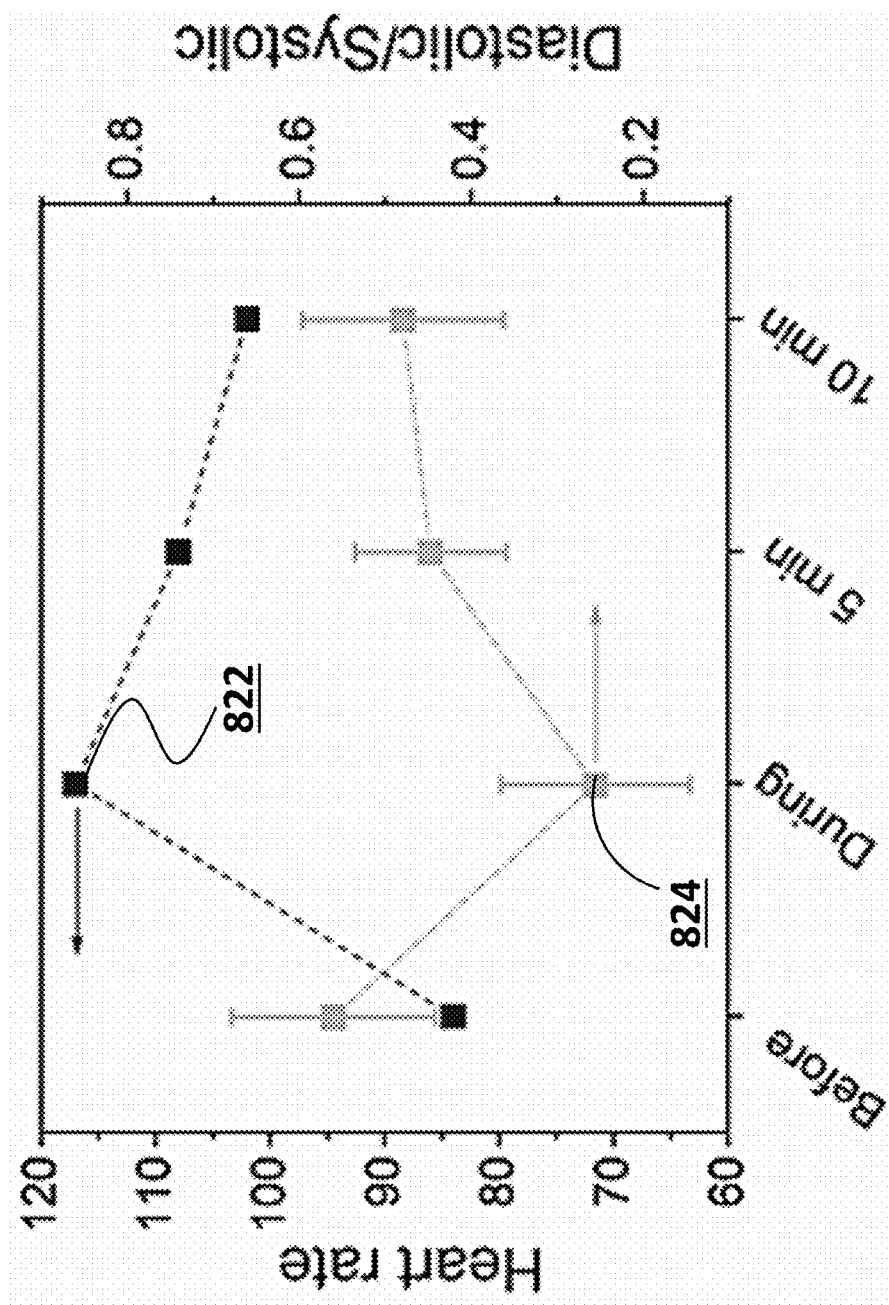

Behavioral patterns that relates to the pulse waveform can be also potentially measured with a sensing patch. Here, we illustrate the meaningful effects on the pulse waveform as a consequence of smoking. Generally, smoking has long term effect and short time effect on pulse waveform features, such as atrial stiffness, pulse wave velocity and more. As can be seen in FIG. 8D, the waveform before (822) and during (824) smoking are substantially different. The time length during smoking is shorter which implies the heart rate increases. Yet, increased heart rate can be a result of many external parameters like excitement or exercise. Additional discrimination parameter is the ratio between the systolic and the diastolic amplitude. Combination of these parameters can help to specifically determine behaviors of the wearer.

Referring to FIGS. 8A-8E: several proofs of concepts that are demonstrated with GNP sensing patch. 8A—Applying an algorithm for beats per minutes (BPM) calculation on waveforms that were recorded from a PPG sensor and from the GNP sensing patch ($R^2 > 0.99$). 8B—General scheme for the waveform contour and the main parameters that can be extracted from it. 8C—Correlation between the systolic—diastolic peak in the waveform measured with GNP sensing patch to the diastolic BP measured by arm cuff blood pressure monitor (from Rossmax). Different colors stand for different subjects. 8D—the pulse waveform recoded from GNP sensing patch for one subject before smoking and after smoking. 8E—the heart rate (822) and the systolic amplitude divided by the diastolic amplitude (824) during different steps of smoking. The error bars stand for the standard deviation calculated from 30 waveforms.

The heart rate variability (HRV) is a highly studied parameter that is used to assess the breathing rate and as reliable reflection of the many physiological factors. We have extracted the HRV from the pulse waveform recorded by the GNP sensing patch from the wrist (FIG. 9A—graph 910) and compared it to the HRV measured with Polar H7 chest strap. The waveform was recorder with a frequency of 160 samples per second (sps). Mainly, the waveform derivative was used and the time differences from peak to peak, $\Delta t$, were calculated (see FIG. 9B—curve 920). $\Delta t$ from peak to peak represent the HRV and presented as a function of samples in FIG. 9C (graph 930). The results obtained from the GNP sensing patch show similar trend to the result from the Polar H7 chest strap. The correlation is presented in FIG. 9D (graph 940). The high correlation provides a good indication that the HRV values can be measured with a wearable wrist band or patch based on GNPs.

Referring to FIGS. 9A-9d. 9A illustrates a sample of pulse waveforms that was recorded by the GNP sensing patch. 9B illustrates the derivative values that were calculated from the waveform. The sharp peaks were used to calculate the HRV. 9C illustrates the HRV that was calculated from the GNP sensing patch (blue) and from Polar H7 chest strap. 9D illustrates the correlation between the HRV extracted from Polar H7 chest strap and from the GNP sensing strip ($R^2 > 0.99$).

Measuring the Pulse Waveform from Different Body Locations

Figure 10:
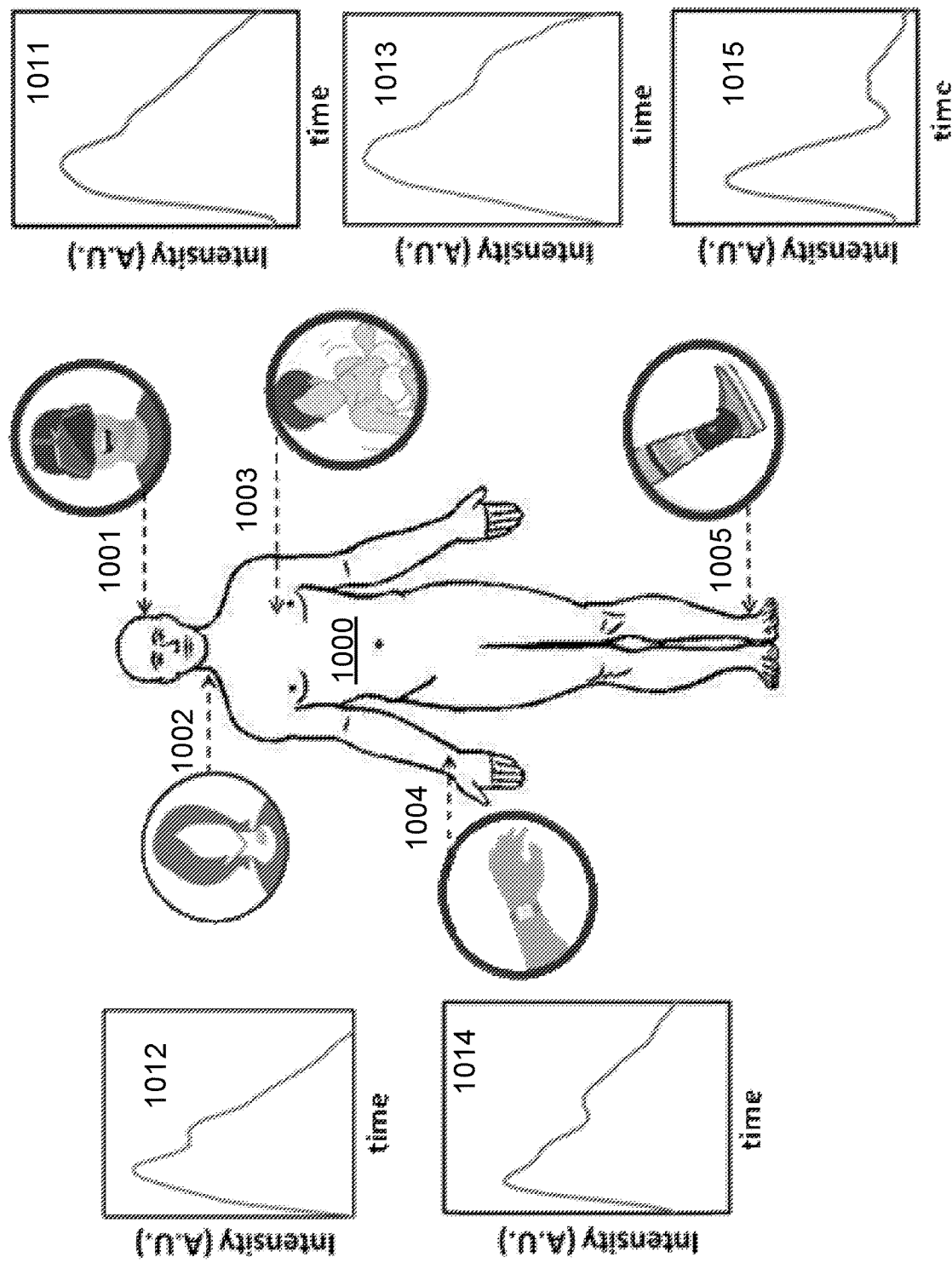
FIG. 10 illustrates various positions of a sensing device and various waveforms according to an embodiment of the invention.

FIG. 10 illustrates several body locations (1001, 1002, 1003, 1004, 1005) in which measurement were made of the pulse waveform and a representative waveform (see measurements 1011, 1012, 1013, 1014 and 1015) from each location taken from the same subject. As can be noticed, there are some differences in the waveform contour at different body locations.

The icons near the body location indicate possible application where the GNP sensing patch can be embedded in. Specifically, measuring the pulse waveform in the head (temporal artery) can be implanted in googles. This can be used for virtual reality (VR) goggles for enhanced gaming applications. The game can respond to the biometric data recorded and change accordingly. For example, when the gamer is excited, the heart rate will increase, the game can respond accordingly by choosing the next game scene the will continue to excite the user. By recoding the biometric data of VR user, big data analytics can be used to learn the user's responses to different situation. Biometric data collection from goggles is also relevant for sport in which googles are in use, such as skiing.

The pulse waveform recorded from the neck (carotid artery) is of strong amplitude due to the proximity of the artery to the skin. This can be used for clinical application were high resolution waveforms are required. The pulse waveform recorded from the chest (apical pulse) can be integrated in smart bras, shirts, or patches. The pulse waveform recorded from the wrist (radial artery) can be embedded in smart watches or wristbands. The pulse waveform recorded from the leg (both, posterior tibial artery and dorsalis pedis artery) can be integrated in socks and shows. The monitoring of blood flow to the foot is of high importance for diabetes patients.

The ability to measure the pulse waveform in several body locations simultaneously allows measuring of additional parameters like the pulse wave velocity (PWV). This parameter is described as the time it takes ($\Delta t$) to the pulse to propagate along the arteries when measured in two locations with a known distance between them ($\Delta x$). PWV is a well-studied parameter and it is associated with many diseases. Generally, the PWV increases proportionally to the number of cardiovascular risk factors present. Here we preset the possibility to remotely measure the PWV with wearable sensors. When using and array of sensors, the PWV can also be measures locally, from on artery. This proof of concept was demonstrated using two MEMS pressure sensors. The PWV is highly correlated to the blood pressure and is a key parameter in the development of a cuff-less blood pressure monitor. It should be noted that the sampling rate required in order to measure local PWV with an example (relatively high) value of 10 m/sec[47] with characteristic distance of 20 mm between the sensors is about 500 sps. The presented GNP sensing patch is capable of measuring at these frequencies because of the quantum mechanical transduction mechanism that is many orders of magnitude faster.

Body Movements Related Noises

Figure 12:
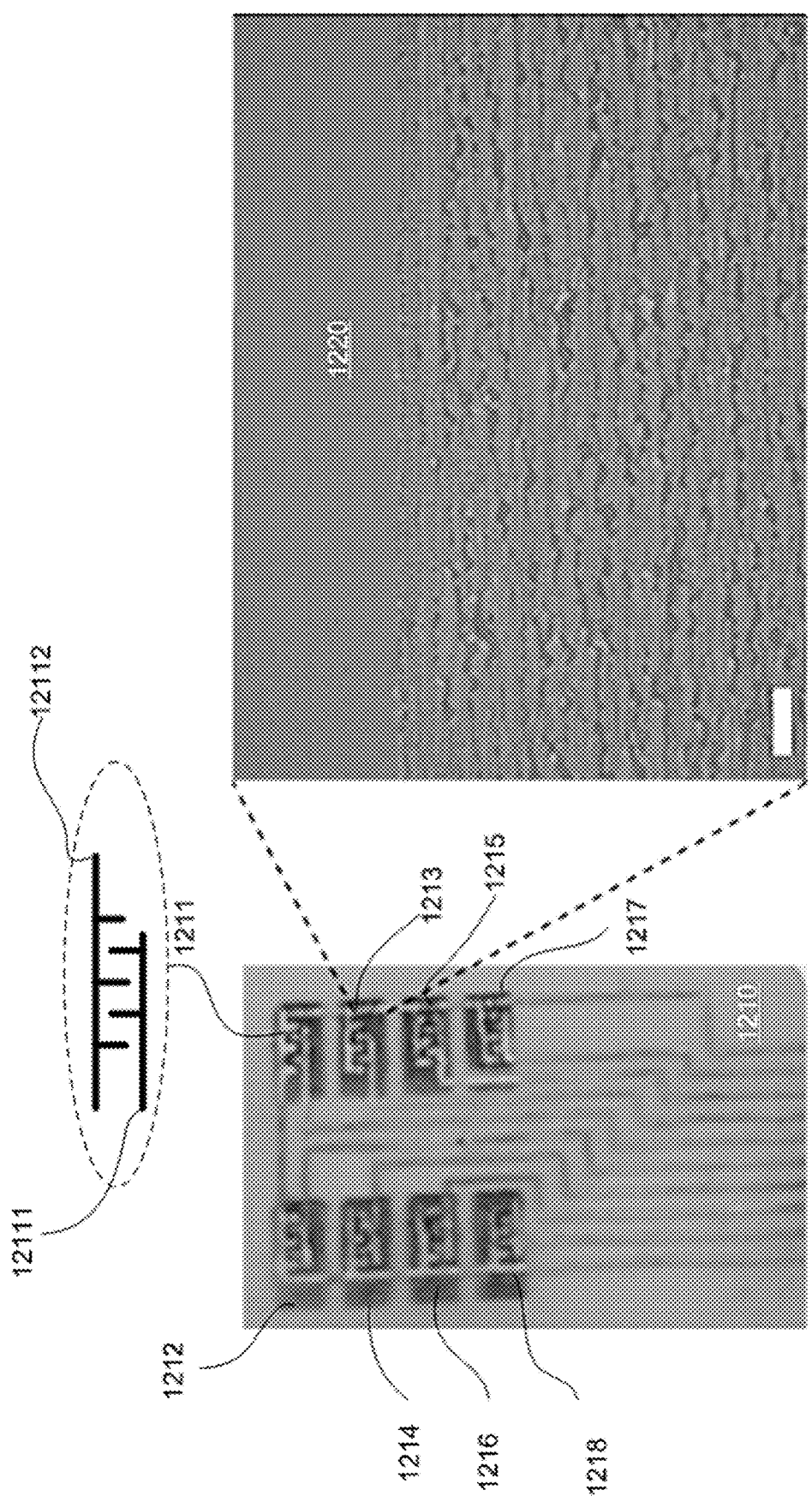
FIG. 12 illustrates sensing elements according to an embodiment of the invention.

Noises due to body movements are a major concern for wearable sensors. This topic is handles mainly with signal processing approaches in PPG sensors. Those tools are least effective if the movement has a periodical nature, in which the movement signal can be misread as the pulse signal (especially for periodical movements that have a similar frequency as the pulse, such as typing, walking, or running) Here, we approach this problem by integration of an array of sensors. The simple production route and the low production cost of the GNP sensing patch enable realization of this concept. In strain sensing concept for measuring the pulse waveform, the pulse and noises due to body related noises affect the sensors response in a similar manner—change in the electrical resistance on the sensor. As presented in FIG. 11A, the design of the GNP sensing patch (1100) has 8 sensors (each sensor may have two sensing elements) that are adhered to the skin and fixed by a wristband (see FIG. 12 for a full picture of the sensing patch). This configuration ensures, statistically, that at least one senor will be located on the artery (for example, the sensor in the light blue circle) while at least another sensor will be located near the artery (for example, the sensor in the dark blue circle). The last does not sense the pulse waveform, yet, it senses the body movements in a similar manner to the sensors that is located on the artery. The main advantages in using an array of sensor can be classified as following:

The ability to choose the sensor that is best located on the artery and is less sensitive to movements (FIG. 11B—see reading of GNP sensor 1111 and readings of movement sensor 1112). Similar results were obtained for 3 different subjects for light movements when the GNP sensing array was located on the wrist and on the head.

Some movements have an effect on all sensors in the GNP sensing patch. In this case, the movement sensor can detect the movement and signal the system not to account for the pulse waveform measurements at that specific time. This feature has great significance when the movements are in a similar frequency to the pulse (see FIGS. 11C and 11D). FIG. 11C—reading of GNP sensor 1121 and readings of movement sensor 1122. FIG. 11D—reading of GNP sensor 111 and readings of movement sensor 1112

Referring to FIGS. 11A-11D. 11A—the GNP sensing patch adhered to the skin and fixed under a wrist band. In the eight sensors array configuration, one sensor will probably be located on the artery (for example the sensor in the light blue circle) and other sensor will probably be located nearby so it will sense mainly the body movements (for example, the sensor in the dashed dark blue circle). 11B—one minute of light hand movements wherein one sensor (light blue) detects mainly the pulse waveform and another sensor (dashed dark blue) detects mainly the hand movements. 11C and 11D—the response of both, the pulse waveform sensor, and the movements sensor to a strong wrist banding.

Signal Processing

Normalizing the signal: the pulse waveform signal was normalized between 0 to 1 by the following:

$$Intensity = \frac{R_i - minmun(R_i:R_{i+j})}{maximum(R_i:R_{i+j}) - minmun(R_i:R_{i+j})}$$

Where $R_i$ is the measured resistance at a point of time, i, $R_j$ is the measured resistance at a point of time, j. j–i is the time it takes to complete one waveform (from 0.3 to 1 sec, depending on the person).

Heart rate: The sensor is selected by visual observation of the pulse waveform from the signal obtained from the GNP sensing array. In practice, the sensor that has been chosen is the one that is located on the artery and can sense the pulse waveform. A derivative was applied on the pulse waveform. Each heartbeat was identified with a sharp peak in the derivative (see FIG. 3b). A threshold value for the derivative intensity was set and the peaks that have crossed this value are counted. The number of beat per minuets is displayed.

Correlation to diastolic blood pressure: The pulse wave signal collected from both, the GNP sensing patch and the finger cuff PPG sensor where normalized as detailed above than the diastolic peak (FIG. 8b) was subtracted from the systolic peak (FIG. 8b). The resulted values from the two devices were compared and correlated to the diastolic plod pressure that was measured in the same time with arm cuff monitor.

Heart rate variability: A derivative was applied on the pulse waveform. Each heartbeat was identified with a sharp peak in the derivative (see FIG. 8b). A threshold value for the derivative intensity was set. The time difference between the peaks that have crossed this value was calculated and displayed as the heart rate variability.

Body movements related noises: the pulse waveform sensor (e.g., the sensors in the GNP array that is located on the artery) and the movement sensor (e.g., the sensors in the GNP array that is located near the artery so it doesn't sense the pulse but it senses the movements in a similar manner to the pulse waveform sensor) are chosen. The signals are adjusted so that the movements signal will have similar amplitude. The adjustment is done by simple means of multiplying the signal with a real number. Then the signal of the movement sensor is subtracted from the signal of the pulse waveform sensor.

Regional PWV is measured using at least two sensors in different body locations. The distance between the body locations is measured separately. This value is specific for each person and defined as Δx (for example, the distance between the carotid artery in the neck to the radial artery in the wrist). The pulse waveform is measured for the two different body locations at the same time. The time differences between the waveform peaks is measured and defined as Δt (see figure). The PWV is $$PWV = \frac{\Delta x}{\Delta t}$$

defined as:

Local PWV is measured using at least two sensors from the same artery. In this case, two sensors in the same GNP sensing array can be used.

Figure 13:
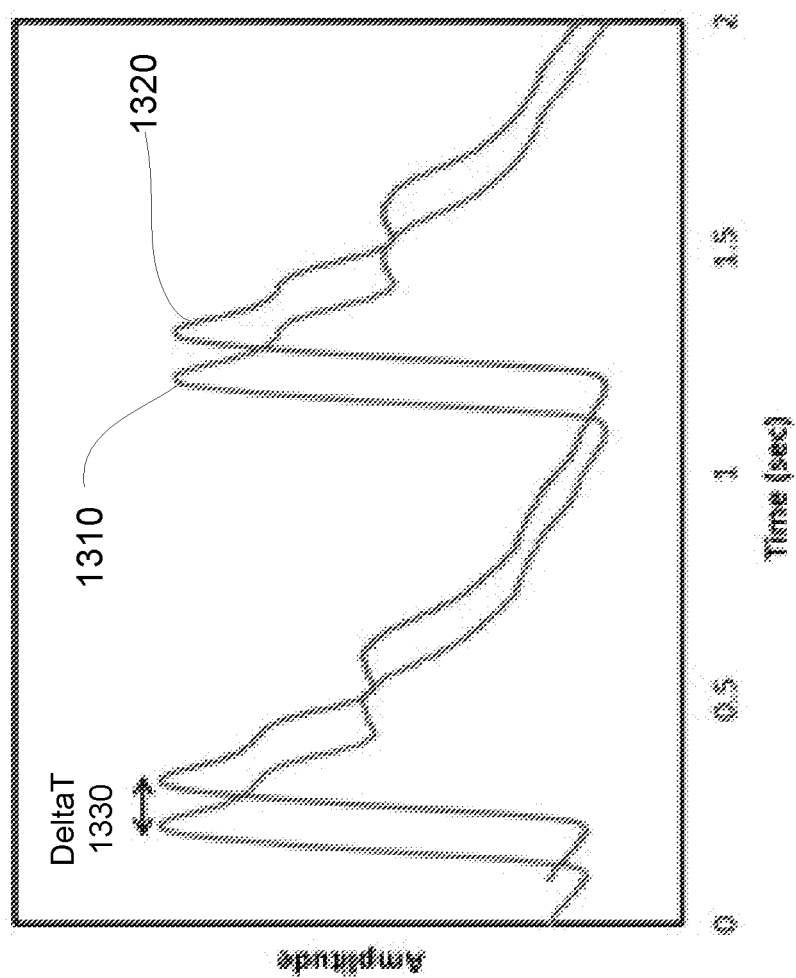
FIG. 13 illustrates various waveforms according to an embodiment of the invention.

FIG. 13 illustrates sensing signals from a pair of spaced apart sensing elements.

GNP sensing patches with high reproducibility were presented as highly sensitive strain/pressure sensors. The GNP sensing patches were realized as wearable sensors for digital health applications. The pulse waveforms recorded with this sensor is comparable to clinically grade finger cuff PPG sensor. Several physiological parameters were calculated form the waveform and compared to finger cuff pulse oximeter and to chest strap. The measure physiological parameter included heart rate, changes in blood pressure and HRV—all were in excellent agreement with the compared reference. The GNP sensing patch sense the pulse waveform in multiple body locations which is promising for a large span of potential applications ranging from VR to clinical applications. In addition, the measurement of the pulse waveform from several body locations is a promising tool for wearable PWV sensors. Finally, noises that are related with body movement were handled by choosing the sensor in the sensing patch that is less prone to movement and using movements reference sensors for mathematical noises reduction.

The next generation of such sensors will allow monitoring additional physiological parameters like body temperature and dehydration while considering environmental effects such as temperature and humidity. Another aspect is wireless communication and power consumption. The developed technology has low power consumption and therefore enables operation of the devise for a few days with a small "coin" battery.

Experimental Methods

GNPs Ink Synthesis

Gold (III) chloride trihydrate (HAuCl4.3H2O), tetraoctylammonium bromide (TOAB), sodium borohydride, and Hexanethiol were purchased from Sigma-Aldrich. A solution of HAuCl4 was added to a stirred solution of TOAB in toluene. After stirring 10 min, the lower aqueous phase was removed. Organic ligands and sodium borohydride were subsequently added to the toluene phase. After 3 hours at ice temperature, the lower aqueous phase was removed and the toluene phase was subsequently evaporated by rotary evaporation. After first washing with cold ethanol, the solution was kept at 5° C. for 18 h until achieving complete precipitation. The dark-brown precipitate was filtered off and washed with ethanol. The procedure was repeated three times to remove all leftover ions such as TOAB.

Printing Flexible, Skin Attachable Pulse and Movement Sensors

Following the gold nanoparticles (GNPs) ink synthesis, the sensor is fabricated using sciFLEXARRAYER S3 printer (from: Scienion). Silver conductive ink (commercial) was printed first on a flexible substrate (drop size of ~500 picoliter, 125 µm spacing between droplets) and sintered for a couple of hours in—300° C. The GNP ink was printed as the sensing layer on top of the silver electrodes (drop size of ~300 picoliter, 50 µm spacing between droplets)—an optic image of the sensing patch is presented in FIG. 13. The resulted sensors had a baseline resistance of ~20 MΩ and Gauge Factor (e.g., the sensitivity to strain) of ~50.

Annealing process are induced in order to enhance the sensor sensitivity towards small strains in the range that are generated by the human pulse.

Specifically, using the processes that are mentioned below, the Gauge Factor is enhanced from 50 to ~200 and the baseline resistances of the sensors decrease to ~0.5 MΩ.

The sensing film is then covered with a biocompatible protection layer (e.g., Polydimethylsiloxane). The sensor is connected to a custom made printed circuit board (PCB) as the electric circuit. This PCB can also contain a Bluetooth connection. This prototype is tested for pulse waveform sensing while been exposed to different types of noises.

FIG. 13—left, optic image of the GNP sensing patch. Each sensing pixel is 1×3 mm Right, optic image of printed GNP ink on Kapton (scale bar=400 µm).

Post Printing Processes

Option 1: thermal post printing process was performed. The sensors were placed on a hot plate (185° C.) for 30-40 minutes.

Option 2: Photonic sintering process was applied. The sensors were placed in the benchtop SINTERON 500 systems from Xenon Corp the applied voltage was 470 Joules, the distance from the ultraviolet lamp was 45 mm above the GNP sensing patch and was placed in the center of the lamp. Tens of pulses were used. The process was done in room temperature. The system provided pulses in a frequency of 3 pulses per second. This is just a non-limiting sintering process. Other systems may be used during the photonic sintering, other distances and/or temperatures and/or pulses duration and/or pulses number and/or pulses rate and/or other voltages may be used. A single pulse of variable or fixed duration may be used.

The sintering process increases the nanoparticles effective size—thereby increasing the sensitivity of the sensing elements.

The relevant formula: $GF=\beta(D+l)$

GF is the gauge factor, $\beta$ is the tunneling constant, D is the particles diameter and l is the distance between the particles.

The sintering process may be executed with or without feedback. For example—the resistance may be measured and when reaching the desired resistance, the sintering process may end.

The feedback may involve imposing stress on the sensing element-such as bending, stretching or any other deformation may be applied. For example—performing a three different (or any other number) of bending. The resistance can be made per each bending to determine the change is the resistance as a function of bending. The bending is translated to strain and then the gauge factor can be estimated (the response to strain divided by the strain).

There are several advantages for photonic sintering:

The process is done in room temperature. Many temperature sensitive polymers and other substrates can be used.

The process is very fast—about 3 pulses are emitted per second.

When using an array of sensors, each sensor can be sintered selectively be covering several sensors and exposing other sensors with a dedicated shadow mask.

The post printing processes and the consequent enlargement of nanoparticles affect the sensing properties of the device. The resistance of nanoparticles film decreases with increasing post printing processes time, which corresponds to effective enlargement of nanoparticles. The control over the resistance will be achieved by controlling the period of times for the post printing processes. In order to use conventional measuring instruments for real world applications, this controlled decrease in resistance is required. As a consequence of the different post printing processes, different properties and sensitivities of the devices can be achieved. For example, partial sintering at a controlled temperature and for short time (tens of minutes) will enhance the sensitivity to strain/pressure so the sensors will be more sensitive to subtle pressures.

After the photonic sintering the sensing film is then covered with a thin film (for example—50 µm) of biocompatible protection layer (e.g., Polydimethylsiloxane). The sensor is connected to a printed circuit board (PCB)—or any other electrical and/or mechanical entity—the PCB may support the electrical circuits that act as a sensing circuit. This PCB can also contain a Bluetooth connection. This prototype is tested for pulse waveform sensing while been exposed to different types of noises.

Sensors Readings

The sensors reading was collected via a costume designed printed circuit board (PCB) (from: JLM innovation). The communication was done with a BLE protocol that was developed by shrewd: things. The sampling rate was 20 sps per sensors when all 8 sensors were measured and 160 sps when one sensing element in the sensing patch was chosen in order to get high resolution waveform.

There were provided sensors and methods that
 a. Measure the pulse waveform with strain/pressure sensors based on nanoparticles with accuracy similar to finger cuff PPG sensor.
 b. Enable extraction of biometric and behavioral data for the pulse waveform measured by with strain/pressure sensors based on nanoparticles.
 c. Measure the pulse waveform with strain/pressure sensor from different body locations (different arteries).
 d. Use the measured pulse waveform with strain/pressure sensor based on nanoparticle from several body location to measure parameters like pulse wave velocity.
 e. Use an array of sensors to reduce the need to accurately locate the sensor on the artery.
 f. Use an array of sensors to enable the selection of a sensor/s the gives the most accurate and high signal of the pulse waveform at rest and during movements.
 g. Perform calibration of body movement related noise with neighboring strain/pressure sensors.
 h. Provide an identification mechanical movement events of the skin that inflict noise to pulse waveform readings.
 i. Use an array of strain/pressure sensor based on nanoparticles to measure the local pulse wave velocity.

Figure 14:
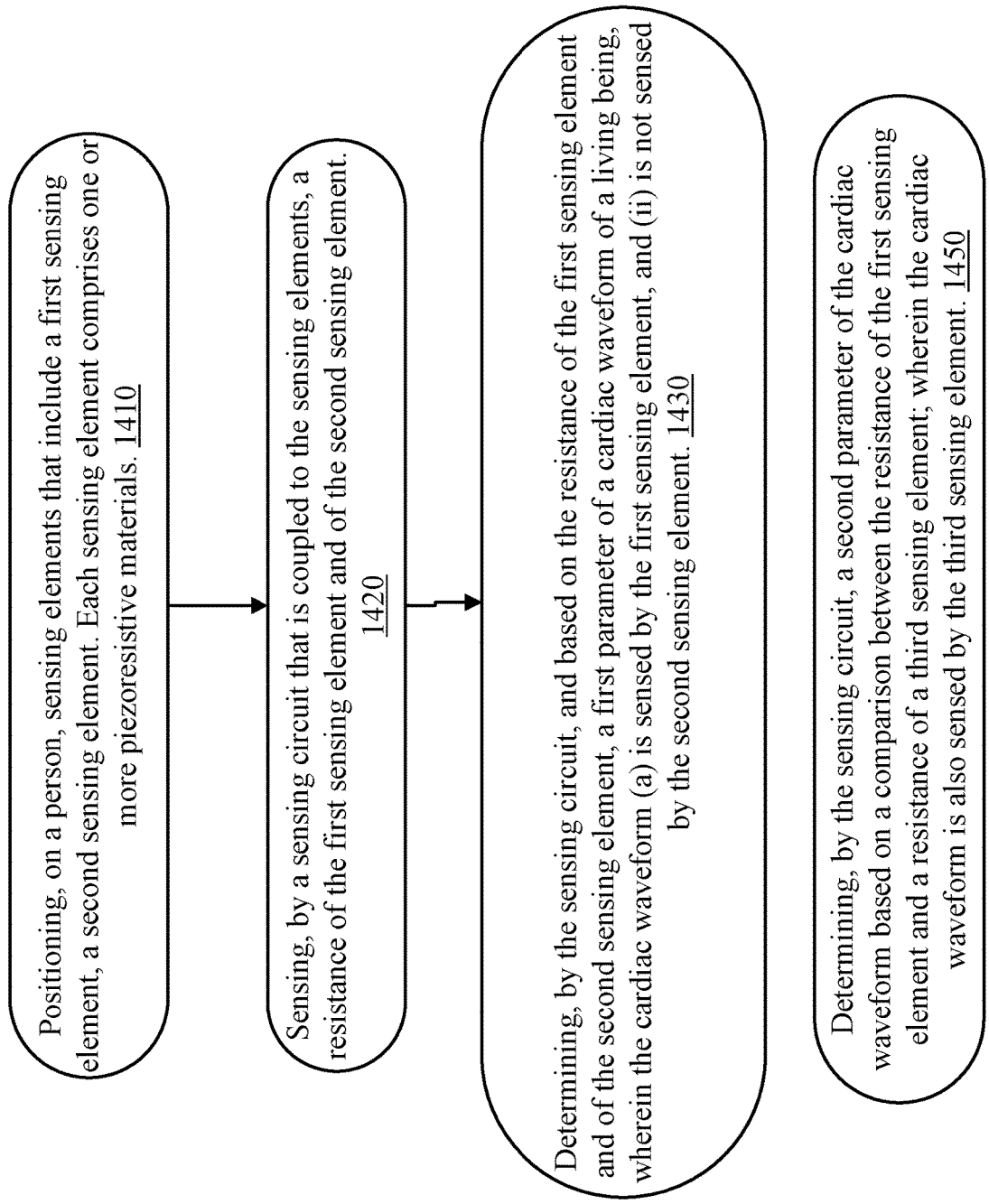
FIGS. 14-16 illustrates examples of methods.
Figure 15:
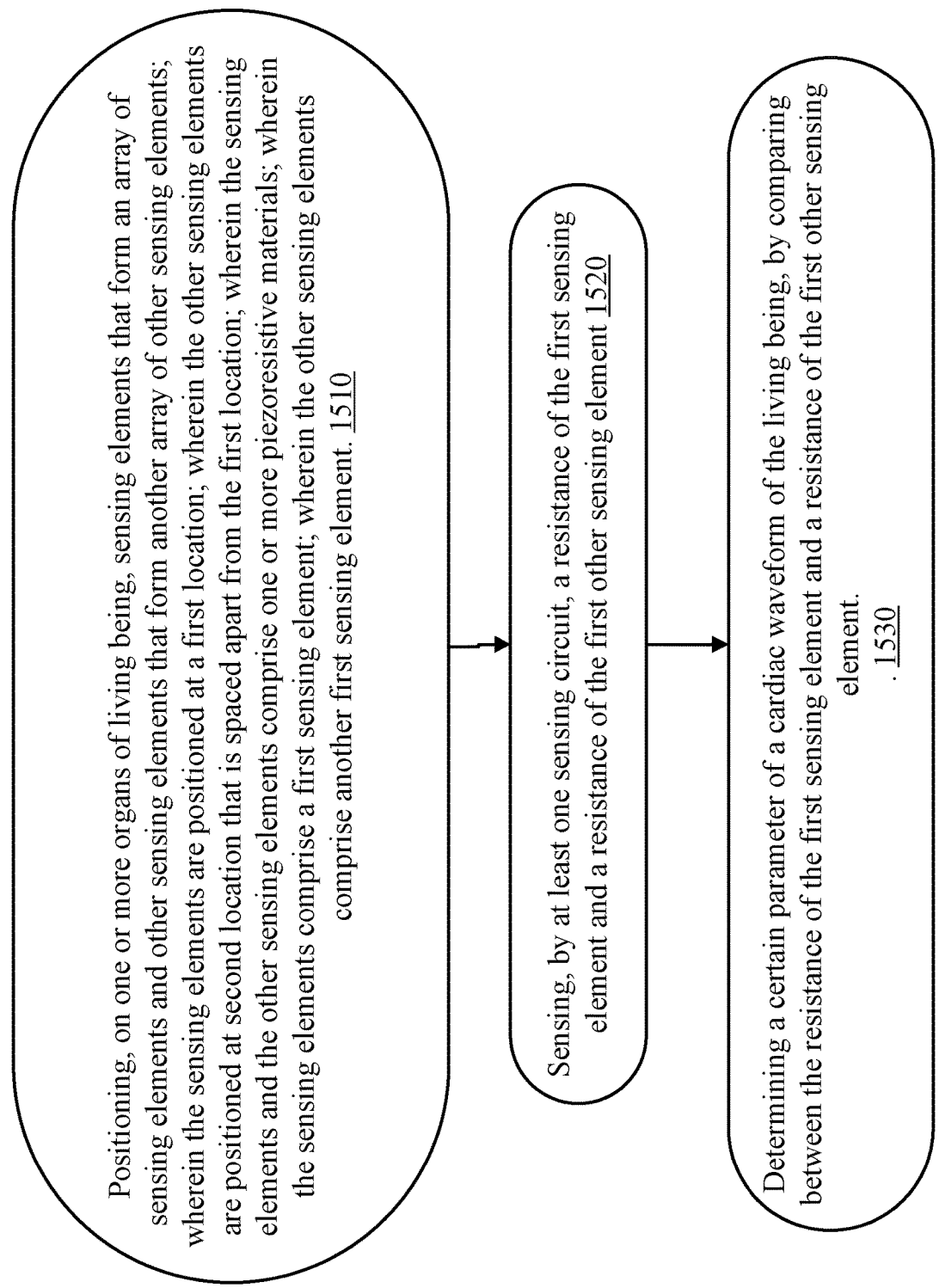

FIG. 14 illustrates method 1400.

Method 1400 may include sensing one or more parameters of one or cardiac waveform based on signals provided by any of the mentioned sensing devices illustrate din the specification and/or the drawings. A parameter of a cardiac waveform may be driven directly or indirectly from the cardiac waveform. The parameter of the cardiac waveform may reflect the health of the monitored person.

Method 1400 may start by step 1410 of positioning, on a person, sensing elements that include a first sensing element, a second sensing element. Each sensing element comprises one or more piezoresistive materials.

Step 1410 may be followed by step 1420 of sensing, by a sensing circuit that is coupled to the sensing elements, a resistance of the first sensing element and of the second sensing element. The sensing may occur during one or more measurement periods. The duration of a time window may be a fraction of a second, a second or more than a second.

Step 1420 may be followed by step 1430 of determining, by the sensing circuit, and based on the resistance of the first sensing element and of the second sensing element, a first parameter of a cardiac waveform of a living being, wherein the cardiac waveform (a) is sensed by the first sensing element, and (ii) is not sensed by the second sensing element.

Step 1430 may include compensating for movements of the living being by comparing between (a) the resistance of the second sensing element, and (b) at least one out of the resistance of the first sensing element and the resistance of the third sensing element.

It is noted that step 1430 may be executed by a device or component that receives information about the outcome of step 1430 (resistance of first and second sensing elements)—and that device or component (for example a remote computer or server, a smartphone) may be remote from the sensing element.

Method 1400 may also include step 1450 of determining, by the sensing circuit, a second parameter of the cardiac waveform based on a comparison between the resistance of the first sensing element and a resistance of a third sensing element; wherein the cardiac waveform is also sensed by the third sensing element.

It should be noted that there may be a method in which the sensing device is positioned so that both first and second sensing elements may sense the cardiac wave. In this case the method may include determining, by the sensing circuit, and based on the resistance of the first sensing element and of the second sensing element, a parameter of a cardiac waveform of a living being, wherein the cardiac waveform (a) is sensed by the first sensing element, and (ii) is sensed by the second sensing element.

FIG. 1500 illustrates method 1500.

Method 1500 may start by step 1510 of positioning, on one or more organs of living being, sensing elements that form an array of sensing elements and other sensing elements that form another array of other sensing elements; wherein the sensing elements are positioned at a first location; wherein the other sensing elements are positioned at second location that is spaced apart from the first location; wherein the sensing elements and the other sensing elements comprise one or more piezoresistive materials; wherein the sensing elements comprise a first sensing element; wherein the other sensing elements comprise another first sensing element.

Each of said array and other array may be a one-dimensional array, a two-dimensional array and the like. The array and the other array may have the same number of sensing elements, and/or the same shape and/or the same size and/or the same orientation. The array and the other array may differ from each other by at least one of number of sensing elements, shape, size and orientation.

Step 1510 may be followed by step 1520 of sensing, by at least one sensing circuit, a resistance of the first sensing element and a resistance of the first other sensing element.

Step 1520 may be followed by step 1530 of determining a certain parameter of a cardiac waveform of the living being, by comparing between the resistance of the first sensing element and a resistance of the first other sensing element.

Method 1500 may include step 1450.

Figure 16:
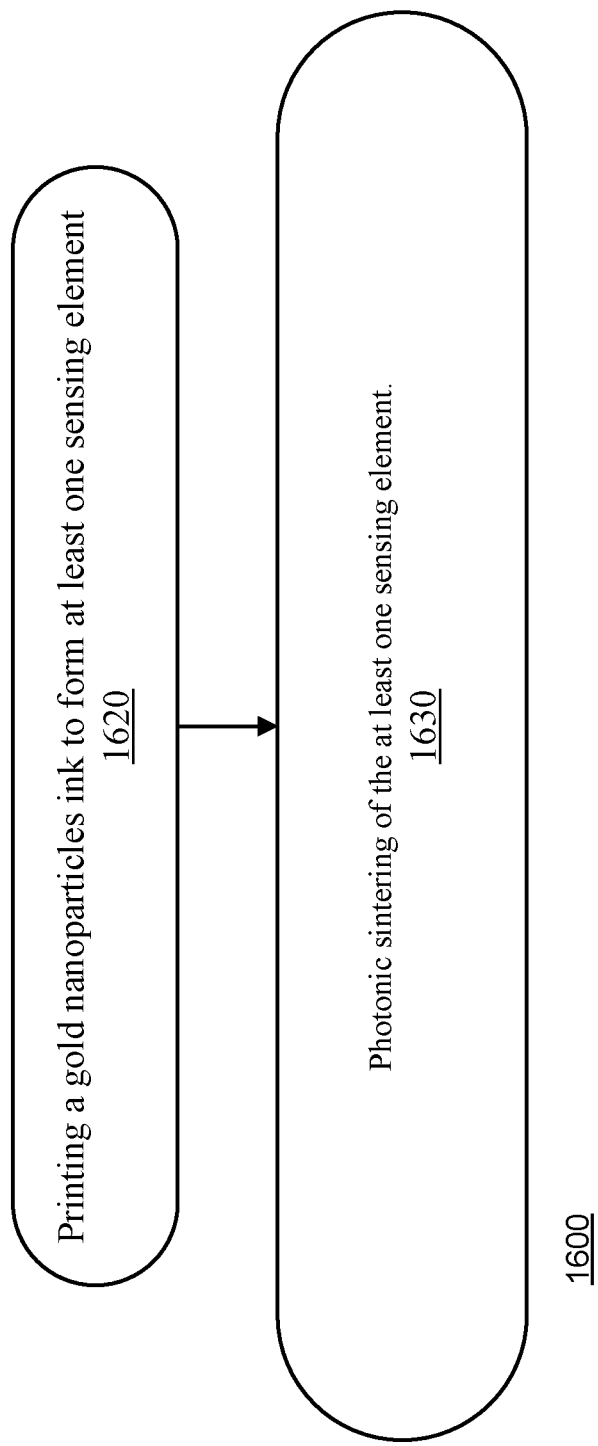

FIG. 16 illustrates method 1600 for manufacturing a gold nanoparticles sensing element. The gold nanoparticles sensing element comprises multiple gold nanoparticles.

Method 1600 may include step 1610 of printing a gold nanoparticles ink to form at least one sensing element. Step 1610 may include or may be preceded by receiving or generating the gold nanoparticles ink—that may be a printable solution or mixture that includes gold nanoparticles.

Step 1610 may be followed by step 1620 of photonic sintering of the at least one sensing element. This increases the sensitivity of the at least one sensing element.

The sintering may be monitored and/or feedback may be provided (such as measuring resistance) in order to obtain the desired properties.

Method 1600 may include additional steps—such as those illustrated in the specification.

Method 1600 is applicable to any other sensing element made of one or more piezoresistive materials.

In the foregoing specification, the invention has been described with reference to specific examples of embodiments of the invention. It will, however, be evident that various modifications and changes may be made therein without departing from the broader spirit and scope of the invention as set forth in the appended claims.

Moreover, the terms "front," "back," "top," "bottom," "over," "under" and the like in the description and in the claims, if any, are used for descriptive purposes and not necessarily for describing permanent relative positions. It is understood that the terms so used are interchangeable under appropriate circumstances such that the embodiments of the invention described herein are, for example, capable of operation in other orientations than those illustrated or otherwise described herein.

The connections as discussed herein may be any type of connection suitable to transfer signals from or to the respective nodes, units or devices, for example via intermediate devices. Accordingly, unless implied or stated otherwise, the connections may for example be direct connections or indirect connections. The connections may be illustrated or described in reference to being a single connection, a plurality of connections, unidirectional connections, or bidirectional connections. However, different embodiments may vary the implementation of the connections. For example, separate unidirectional connections may be used rather than bidirectional connections and vice versa. Also, plurality of connections may be replaced with a single connection that transfers multiple signals serially or in a time multiplexed manner. Likewise, single connections carrying multiple signals may be separated out into various different connections carrying subsets of these signals. Therefore, many options exist for transferring signals.

Although specific conductivity types or polarity of potentials have been described in the examples, it will be appreciated that conductivity types and polarities of potentials may be reversed.

Each signal described herein may be designed as positive or negative logic. In the case of a negative logic signal, the signal is active low where the logically true state corresponds to a logic level zero. In the case of a positive logic signal, the signal is active high where the logically true state corresponds to a logic level one. Note that any of the signals described herein may be designed as either negative or positive logic signals. Therefore, in alternate embodiments, those signals described as positive logic signals may be implemented as negative logic signals, and those signals described as negative logic signals may be implemented as positive logic signals.

Furthermore, the terms "assert" or "set" and "negate" (or "deassert" or "clear") are used herein when referring to the rendering of a signal, status bit, or similar apparatus into its logically true or logically false state, respectively. If the logically true state is a logic level one, the logically false state is a logic level zero. And if the logically true state is a logic level zero, the logically false state is a logic level one.

Those skilled in the art will recognize that the boundaries between logic blocks are merely illustrative and that alternative embodiments may merge logic blocks or circuit elements or impose an alternate decomposition of functionality upon various logic blocks or circuit elements. Thus, it is to be understood that the architectures depicted herein are merely exemplary, and that in fact many other architectures may be implemented which achieve the same functionality.

Any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components. Likewise, any two components so associated can also be viewed as being "operably connected," or "operably coupled," to each other to achieve the desired functionality.

Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

Also for example, in one embodiment, the illustrated examples may be implemented as circuitry located on a single integrated circuit or within a same device. Alternatively, the examples may be implemented as any number of separate integrated circuits or separate devices interconnected with each other in a suitable manner.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first" and "second" are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

We claim:

1. A sensing device, comprising:
a two-dimensional array of nanotechnology-based strain sensing elements, comprising a first sensing element having a sensing mechanism which is based on tunneling and a second sensing element having a sensing mechanism which is based on tunneling; wherein each sensing element comprises one or more piezoresistive materials and has a baseline resistance in the range of 200-500 KΩ, wherein a distance between the first sensing element and the second sensing element exceeds 1 mm, wherein a length and a width of the two-dimensional array exceed 0.5 cm and wherein the two-dimensional array is shaped and sized so that when the sensing device is positioned on an artery, the first sensing element is located on said artery and the second sensing element is not located on said artery; and
a sensing circuit that is coupled to the sensing elements, wherein the sensing circuit is configured to sense a resistance of the first sensing element and of the second sensing element, and to determine, based on the resistance of the first sensing element and of the second sensing element, a first parameter of a cardiac waveform of a living being, wherein the cardiac waveform (a) is sensed by the first sensing element, and (b) is not sensed by the second sensing element.

2. The sensing device according to claim 1 wherein the sensing elements in the array are positioned along a virtual curved line, arranged in a grid, arranged in one or more rows, or arranged in one or more columns.

3. The sensing device according to claim 1 wherein the sensing elements are mounted on a flexible substrate.

4. The sensing device according to claim 1 wherein the array comprises multiple rows and multiple columns of sensing elements.

5. The sensing device according to claim 4 wherein the array comprises eight sensing elements arranged in two rows, wherein the sensing elements have dimensions of 1×3 mm, and wherein there is a spacing of 2 mm between the sensing elements in the same row and the spacing between the rows is 5 mm.

6. The sensing device according to claim 1, wherein the sensing circuit is configured to compensate for movements of the living being by comparing between (a) the resistance of the first sensing element, and (b) the resistance of the second sensing element.

7. The sensing device according to claim 1, wherein the first parameter of the cardiac waveform is selected from the group consisting of a heart rate, heart rate variability, and blood pressure.

8. The sensing device according to claim 1, wherein the array further comprises a third sensing element, wherein the two-dimensional array is shaped and sized so that when the sensing device is positioned on the artery, the third sensing element is located on said artery, and wherein the sensing circuit is configured to determine a second parameter of the cardiac waveform based on a comparison between the resistance of the first sensing element and a resistance of a third sensing element; wherein the cardiac waveform is also sensed by the third sensing element.

9. The sensing device according to claim 8, wherein the second parameter of the cardiac waveform is a pulse wave velocity.

10. The sensing device according to claim 8, wherein the sensing circuit is configured to compensate for movements of the living being by comparing between (a) the resistance of the second sensing element, and (b) at least one out of the resistance of the first sensing element and the resistance of the third sensing element.

11. The sensing device according to claim 1, wherein the one or more piezoresistive materials are metal nanoparticles.

12. The sensing device according to claim 1, wherein the one or more piezoresistive materials are nanotubes or nanowires.

13. A method, comprising:
positioning, on a person's artery, a sensing device comprising a two-dimensional array of nanotechnology-based strain sensing elements, comprising at least a first sensing element having a sensing mechanism which is based on tunneling and a second sensing element having a sensing mechanism which is based on tunneling, wherein each sensing element comprises one or more piezoresistive materials comprising metal nanoparticles and has a baseline resistance in the range of 200-500 KΩ, wherein a distance between the first sensing element and the second sensing element exceeds 1 mm, wherein a length and a width of the two-dimensional array exceed 0.5 cm, and wherein the two-dimensional array is shaped and sized so that when the sensing device is positioned on the artery, the first sensing element is located on the artery and the second sensing element is not located on the artery;

sensing, by a sensing circuit that is coupled to the sensing elements, a resistance of the first sensing element and of the second sensing element; and determining by the sensing circuit and based on the resistance of the first sensing element and of the second sensing element, a first parameter of a cardiac waveform of the person, wherein the cardiac waveform (a) is sensed by the first sensing element, and (b) is not sensed by the second sensing element.

14. The method according to claim 13, wherein the sensing elements in the array are positioned along a virtual curved line, arranged in a grid, arranged in one or more rows, or arranged in one or more columns.

15. The method according to claim 13, wherein the array comprises multiple rows and multiple columns of sensing elements.

16. The method according to claim 15, wherein the array comprises eight sensing elements arranged in two rows, wherein the sensing elements have dimensions of 1×3 mm, and wherein there is a spacing of 2 mm between the sensing elements in the same row and the spacing between the rows is 5 mm.

17. The method according to claim 13, wherein the first parameter of the cardiac waveform is selected from the group consisting of a heart rate, heart rate variability, and blood pressure.

18. The method according to claim 13, wherein the two-dimensional array further comprises a third sensing element, wherein the two-dimensional array is shaped and sized so that when the sensing device is positioned on the artery, the third sensing element is located on said artery, and wherein the sensing circuit is configured to determine a second parameter of the cardiac waveform based on a comparison between the resistance of the first sensing element and a resistance of a third sensing element; wherein the cardiac waveform is also sensed by the third sensing element, and wherein the second parameter of the cardiac waveform is a pulse wave velocity.

19. The method according to claim 13, wherein the one or more piezoresistive materials are metal nanoparticles.

20. The method according to claim 13, wherein the one or more piezoresistive materials are nanotubes or nanowires.

* * * * *